US010519218B2

(12) United States Patent
Cottingham et al.

(10) Patent No.: US 10,519,218 B2
(45) Date of Patent: Dec. 31, 2019

(54) SELECTIVE IL-6-TRANS-SIGNALLING INHIBITOR COMPOSITIONS

(71) Applicant: Ferring B.V., Hoofddorp (NL)

(72) Inventors: Ian Cottingham, St-Prex (CH); Daniel Plaksin, St-Prex (CH); Jérémy Duboeuf, Hoofddorp (NL)

(73) Assignee: FERRING B.V., Hoofddorp (NL)

( * ) Notice: Subject to any disclaimer, the term of this patent is extended or adjusted under 35 U.S.C. 154(b) by 0 days.

(21) Appl. No.: 15/532,097

(22) PCT Filed: Dec. 1, 2015

(86) PCT No.: PCT/NL2015/050837
§ 371 (c)(1),
(2) Date: May 31, 2017

(87) PCT Pub. No.: WO2016/089206
PCT Pub. Date: Jun. 9, 2016

(65) Prior Publication Data
US 2018/0282396 A1    Oct. 4, 2018

(30) Foreign Application Priority Data
Dec. 1, 2014    (EP) .................................. 14195726

(51) Int. Cl.
| C07K 14/715 | (2006.01) |
| C12N 15/63 | (2006.01) |
| A61K 38/17 | (2006.01) |
| A61K 38/00 | (2006.01) |

(52) U.S. Cl.
CPC .......... C07K 14/7155 (2013.01); C12N 15/63 (2013.01); *A61K 38/00* (2013.01)

(58) Field of Classification Search
None
See application file for complete search history.

(56) References Cited

U.S. PATENT DOCUMENTS

| 4,751,180 | A | 6/1988 | Cousens et al. |
| 5,457,035 | A | 10/1995 | Baum et al. |
| 5,783,672 | A | 7/1998 | Mosley et al. |
| 6,605,703 | B1 | 8/2003 | Schaeffer et al. |
| 6,838,076 | B2 | 1/2005 | Patton et al. |
| 6,887,687 | B2 | 5/2005 | Anderson |
| 7,534,862 | B2 | 5/2009 | Seegert et al. |
| 7,629,147 | B2 | 12/2009 | Seegert et al. |
| 7,851,182 | B2 | 12/2010 | Seegert et al. |
| 8,895,012 | B2 | 11/2014 | Watzig et al. |
| 9,034,817 | B2 | 5/2015 | Watzig et al. |
| 9,573,989 | B2 | 2/2017 | Watzig et al. |
| 2002/0012962 | A1 | 1/2002 | Stahl et al. |
| 2003/0118510 | A1 | 6/2003 | Patton et al. |
| 2007/0270334 | A1 | 11/2007 | Seegert et al. |
| 2008/0227155 | A1 | 9/2008 | Seegert et al. |

| 2010/0028367 | A1* | 2/2010 | Watzig ................. A61K 38/204 424/178.1 |
| 2014/0178378 | A1 | 6/2014 | Watzig et al. |
| 2015/0361157 | A1 | 12/2015 | Watzig et al. |
| 2017/0320932 | A1 | 11/2017 | Cottingham et al. |

FOREIGN PATENT DOCUMENTS

| DE | 19941897 A1 | 3/2001 |
| EP | 0442724 A2 | 8/1991 |
| EP | 1148065 A1 | 10/2001 |
| EP | 1491554 A1 | 12/2004 |
| EP | 1630232 A1 | 3/2006 |
| EP | 1801121 A1 | 6/2007 |
| WO | WO-94/12520 A1 | 6/1994 |
| WO | WO-95/33059 A2 | 12/1995 |
| WO | WO-00/18932 A2 | 4/2000 |
| WO | WO-01/58957 A2 | 8/2001 |
| WO | WO-03/008454 A2 | 1/2003 |
| WO | WO-2004/113383 A2 | 12/2004 |
| WO | WO-2006/021453 A2 | 3/2006 |
| WO | WO-2007/071449 A1 | 6/2007 |
| WO | WO-2008/000516 A2 | 1/2008 |
| WO | WO-2009/049881 A1 | 4/2009 |
| WO | WO-2016/087941 A1 | 6/2016 |

OTHER PUBLICATIONS

Scheller et al, Seminars in Immunology; 2014, vol. 26; pp. 2-12.*
Luig et al Journals of the American Society of Nephrology; 2015; vol. 26; pp. 1597-1607.*
Al-Gwaiz, L.A. and Babay, H.H., The Diagnostic Value of Absolute Neutrophil Count, Band Count and Morphologic Changes of Neutrophils in Predicting Bacterial Infections, Med. Princ. Pract., 16: 344-347 (2007).
Ancey et al., A fusion protein of the gp130 and interleukin-6Ralpha ligangbinding domains acts as a potent interleukin-6 inhibitor, J. Biol. Chem., 278(19):16968-16972 (2003).
Atreya et al., Blockade of interleukin 6 trans signaling suppresses T-cell resistance against apoptosis in chronic intestinal inflammation: Evidence in Crohn disease and experimental colitis in vivo, Nature Medicine, 6(5):583-588 (2000).
Barkhausen et al., Selective blockade of interleukin-6 transsignaling improves survival in a murine polymicrobial sepsis model, Crit. Care Med., 39(6):1407-1413 (2011).
Bayliss et al., A humanized anti-IL-6 antibody (ALD518) in non-small cell lung cancer, Expert Opin. Viol. Ther. Early Online, pp. 1-6 (Oct. 17, 2011).
Becker et al., TGF-β Suppresses Tumor Progression in Colon Cancer by Inhibition of IL-6 trans-Signaling, Immunity, 21:491-501 (2004).
Bitter et al., Expression and Secretion Vectors for Yeast, Methods in Enzymology, 153:515:545 (1987).
Boulanger et al., Hexameric Structure and Assembly of the Interleukin-6/IL-6 α-Receptor/gp 130 Complex, Science 300:2101-2104 (2003).
Boulanger et al., Hexameric Structure and Assembly of the Interleukin-6/IL-6 α-Receptor/gp 130 Complex, Science 300:2101-2104 (2003). Supplemental Information. Materials & Methods, 5 pages (2003).

(Continued)

*Primary Examiner* — Bridget E Bunner
(74) *Attorney, Agent, or Firm* — Brenda H. Jarrell; Rolando Medina; Choate, Hall & Stewart, LLP

(57) ABSTRACT

A selective IL-6-trans-signalling inhibitor can be used to treat a variety of IL-6-mediated conditions, including inflammatory diseases and cancer. The inhibitor can safely be administered to humans at a variety of doses.

8 Claims, 11 Drawing Sheets
Specification includes a Sequence Listing.

(56) References Cited

OTHER PUBLICATIONS

Broglie et al., Light-Regulated Expression of a Pea Ribulose-1,5-Bisphosphate Carboxylase Small Subunit Gene in Transformed Plant Cells, Science, 224:838-843 (1984).
Canfield et al., The Binding Affinity of Human IgG for its High Affinity Fc Receptor is Determined by Multiple Amino Acides in the CH2 Domain and Its Modulated by the Hinge Region, J. Exp. Med., 173:1483-1491 (1991).
Chalaris et al., Apoptosis is a natural stimulus of IL6R shedding and contributed to the proinflammatory trans-signaling function of neutrophils, Blood, 110(6):1748-1755 (2007).
Chow et al., A structural template for gp130-cytokine signaling assemblies, Biochimica et Biophasica Acta, 1592(3):225-235 (2002).
Chow et al., In vitro reconstruction of recognition and activation complexes between interleukin-6 and gp130, Biochemistry, 40(25):7593-7603 (2001).
Colbere-Garapin et al., A New Dominant Hybrid Selective Marker for Higher Eukaryotic Cells, J. Mol. Biol., 150:1-14 (1981).
Coruzzi et al., Tissue-specific and light-regulated expression of a pea nuclear gene encoding the small subunit of ribulose-1,5-bisphosphate carboxylase, The EMBO Journal, 3(8):1671-1679 (1984).
Cunningham et al., Receptor and antibody epitopes in human growth hormone identified by homolog-scanning mutagenesis, Science, 10(4896):1330-1336 (1989).
Cunningham et al., High-resolution epitope mapping of hGH-receptor interactions by alanine-scanning mutagenesis, Science 244(4908):1081-1085 (1989).
Darnell, Jr., STATs and Gene Regulation, Science, 277:1630-1635 (1997).
Deisenhofer, Crystallographic Refinement and Atomic Models of a Human Fc Fragment and Its Complex with Fragment B of Protein A from *Staphylococcus aureus* at 2.9- and 2.8-A Resolution, Biochem., 20(9):2361-2370 (1981).
Duncan et al., Localization of the binding site for the human high-affinity Fc receptor on IgG, Nature, 332:563-564 (1988).
EBI Accession No. AAY92205, Fusion polypeptide 616, IL-6 trap (Aug. 1, 2000).
EBI Accession No. AEF92945, Wild-type egp130fc, Seq ID: 11 #2 (May 4, 2006).
Eck et al., Goodman & Gilmans The Pharmacological Basis of Therapeutics, Ninth Edition, McGraw-Hill, pp. 77-101 (1996).
Economides et al., Cytokine traps: multi-component, high-affinity blockers of cytokine action, Nature Medicine, 9(1):47-52 (2003).
Economides et al., Designer Cytokines: Targeting Actions to Cells of Choice, Science, 270:1351-1353 (1995).
Edwards et al., The Formation of a structure with the features of synovial lining by subcutaneous injection of air: an in vivo tissue culture system, J. Pathology, 134:147-156 (1981).
Engelhard et al., The insect tracheal system: A conduit for the systemic spread of Autographa califonica M nuclear polyhedrosis virus, Proc. Natl., Acad. Sci., 91:3224-3227 (1994).
Fingl et al., The Pharmacological Basis of Therapeutics, Goodman Gilman Eds. Macmilliam Publishing Co., pp. 1-46 (1975).
Fischer et al., A bioactive designer cytokine for human hematopoietic progenitor cell expansion, Nature Biotechnology, 15:142-145 (1997).
Friend et al., Phase I Study of an Engineered Aglycosylated Humanized CD3 Antibody in Renal Transplant Rejection, Transplantation, 68(11):1632-1637 (1999).
Fuglsang, Codon optimizer: a freeware tool for codon optimization, Protein Expr. Purif., 2:247-249 (2003).
Gao et al., UpGene: Application of Web-Based DNA Codon Optimization Algorithm, Biotechnol. Prog., 20:443-448 (2004).
Gellissen et al., New yeast expression platforms based on mehtylotrophic Hansenula polymorpha and Pichia pastoris and on dimorphic Arxula adeninivorans and Yarrowia lipolytica—A comparison, FEMS Yeast Research, 5:1079-1096 (2005).

Giese et al., Dimerization of the cytokine receptors gp130 and LIFR analysed in single cells, Journal of Cell Science, 118(21):5129-5140 (2005).
Gomord et al., Biopharmaceutical production in plants: problems, solutions and opportunities, Trends in Biotechnology, 23(11):559-561 (2005).
Goodson et al., Site-Directed Pegylation of Recombinant Interleukin-2 At Its Glygosylation Site, Biotechnology, 8:343-346 (1990).
Grace et al., Structural and Biologic Characterization of Pegylated Recombinant IFN-α2b, Jr. of Interferon and Cytokine Research, 21:1103-1115 (2001).
Greenhill et al., Il-6 Trans-Signaling Modulates TLR4-Dependent Inflammatory Responses via STAT3, J. of Immunology, 186:1199-1208 (2011).
Grotzinger et al., IL-6 Type Cytokine Receptor Complexes: Hexamer, Tetramer or Both?, Biol. Chem., 380:803-813 (1999).
Grotzinger et al., The Family of the IL-6-Type Cytokines: Specificity and Promiscuity of the Receptor Complexes, Proteins: Structure, Function and Genetics, 27:96-109 (1997).
Hammer et al., Increased inflammation and lethality of Dusp1$^{-/-}$ mice in plymicrobial peritonitis models, Immunology, 131:395-404 (2010).
Hartman et al., Two-dominant-acting selectable markers for gene transfer studies in mammalian cells, Proc. Natl. Acad. Sci., 85:8047-8051 (1988).
Herold et al., Anti-CD3 Monoclonal Antibody of New-Onset Type I Diabetes Mellitus, New England J. of Med., 346(22):1692-1698 (2002).
Hobbs et al., Genetic Engineering, McCraw Hill, New York, NY, pp. 191-196 (1992).
Horsten et al., The membrane distal half of gp130 is responsible for the formation of ternary complex with IL-6 and the IL-6 and receptor, FEBS Lett., 360(1):43-46 (1995).
Inoue et al., A highly enhanced thrombopoietic activity by monomethoxy polyethylene glycol-modified recombinant human interleukin-6, J. Lab. Clin. Med., 124(4):529-536 (1994).
International Search Report for PCT/IB2015/002459, 5 pages (dated May 11, 2016).
International Search Report for PCT/NL2015/050837, 7 pages (dated Jun. 2, 2016).
Isaacs et al., Therapy with Monoclonal Antibodies. II The Contribution of fcγ Receptor Binding and the Influence of CH1 and CH3 Domains on In Vivo Effector Function, J. of Immunology, 161:3862-3869 (1998).
Java, Codon Adaptation Tool—JCAT http://www.jcat.de retrieved Oct. 9, 2008.
Jefferis et al., IgG-Fc-mediated effector functions: molecular definition of interaction sites for effector ligands and the role of glycosylation, Immunological Review, 163:59-76 (1998).
Jefferis et al., Interaction sites on human IgG-Fc for FcγR: current models, Immunology Letters, 82:57-65 (2002).
Jefferis et al., Recognition sites on human IgG for Fcγ receptors: the role of flycosylation, Immunology Letters, 44:111-117 (1995).
Jones et al., Loss of CD4 T Cell IL-6R Expression during Inflammation Underlines a Role for IL-6 Trans-Signaling in the Local Maintenance of Th17 Cells, J. Immunol., 184:2130-2139 (2010).
Jostock et al., Immunoadhesins of interleukin-6 and the IL-6/soluble IL-6R fusion protein hyper-IL-6, Jr. of Immunological Methods, 223:171-183 (1999).
Jostock et al., Soluble gp130 is the nature inhibitor of soluble interleukin-6 receptor transsignaling responses, Eur. J. Biochem., 268:160-167 (2001).
Kallen, K.J., The role of transsignaling via the agonistic soluble IL-6 receptor in human diseases, Biochem. Biophys. Acta, 1592:323-343 (2002).
Katre, Immunogenicity of Recombinant IL-2 Modified by Covalent Attachment of Polyethylene Glycol., Jr. of Immunology, 144(1):209-213 (1990).
Kishimoto et al., Interleukin-6 Family of Cytokines and gp130, Blood, 86(4):1243-1254 (1995).
Kohler et al., Continuous cultures of fused cells secreting antibody of predefined specificity, Nature, 256:495-497 (1975).

(56) References Cited

OTHER PUBLICATIONS

Krapp et al., Structural Analysis of Human IgG-Fc Glycoforms Reveals Correlation Between Glycosylation and Structural Integrity, J. Mol. Biol., 325:979-989 (2003).
Krause et al., Rheumatoid arthritis synoviocyte survival is dependent on Stat3, J. Immunol., 169(11):6610-6616 (2002).
Lazar et al., Transforming Growth Factor α: Mutation of Aspartic Acid 47 and Leucine 48 Results in Different Biological Activities, Molecular & Cellular Biol., 8(3):1247-1252 (1988).
Lee et al., Interleukin-6 Induces S100A9 Expression in Colonic Epithelial Cell through STAT3 Activation in Experimental Ulcerative Colitis, PLoS One, 7(9):e38801. doi:10.1371/journal.pone.0038801 (2012).
Levy et al., What does Stat3 do?, J. Clin. Invest., 109(9):1143-1148 (2002).
Lo et al., Il-6 Trans-Signaling in Formation and Progression of Malignant Ascites in Ovarian Cancer, Cancer Res., 71(2):424-434 (2011).
Logan et al., Adenovirus tripartite leader sequence enhances translation of mRNAS later after infection, Proc. Natl. Acad. Sci. USA, 84:3655-3659 (1984).
Lowy et al., Isolation of Transforming DNA: Cloning the Hamster aprt Gene, Cell, 22:817-823 (1980).
Lund et al., Human FcγRI and FcγRII Interact with Distinct But Overlapping Sites on Human IgG1, Journal of Immunology, 147(8):2657-2662 (1991).
Macauley-Patrick et al., Heterologous protein production using the Pichia pastoris expression system, Yeast, 22:249-270 (2005).
Matsumiya et al., Structural Comparison of Fucosylated and Nonfucosylated Fc Fragments of Human Immunoglobulin G1, J. Mol. Biol., 368:767-779 (2007).
Matsumoto et al., Essential Roles of IL-6 Trans-Signaling in Colonic Epithelial Cells, Induced by the IL-6/Soluble-IL-6 Receptor Derived from Lamina Propria Macrophasees on Development of Colitis-Associated Premalignant Cancer in a Murine Model, J. of Immunol., 184: 1543-1551 (2010).
Mees, S.T. et al., Inhibition of Interleukin-6-Transsignaling via gp130-Fc in Hemorrhagic Shock and Sepsis, Journal of Surgical Research, 157(2): 235-242 (2009).
Mikayama et al., Molecular cloning and functional expression of cDNA encoding glycosylation-inhibiting factor, Proc. Natl., Acad. Sci., 90:10056-10060 (1993).
Mitsuyama et al., STAT3 activation via interleukin 6 trans-signaling contributes to ileitis in SAMP1/Yit mice, Gut, 5:1263-1269 (2006).
Mitsuyama, K. et al., Therapeutic Strategies for Targeting the IL-6/STAT3 Cytokine Signaling Pathway in Inflammatory Bowel Disease, Anticancer Research, 27: 3749-3756 (2007).
Murry, L.E., Agrobacterium-Mediated plant transformation in McGraw Hill Yearbook of Science and Technology, McGraw Hill, New York, pp. 191-196 (1992).
Müllberg et al., IL-6 receptor independent stimulation of human gp130 by viral IL-6, J. Immunol., 164(9):4672-4677 (2000).
Nakamura et al., Codon usage tabulated from the international DNA sequence databases, Nucleic Acids Research, 24(1):214-215 (1996).
Nishimoto et al., Anticytokine therapy in autoimmune diseases, Intern. Med., 38(2):178-182 (1999).
Nishimoto, T., A new role of ran GTPase, Biochem. Biophys. Res. Commun., 262(3):571-574 (1999).
Nose et al., Biological significance of carbohydrates chains on monoclonal antibodies, Proc. Natl. Acad. Sci., 80:6632-6636 (1983).
Nowell et al., Therapeutic Targeting of IL-6 Trans-Signaling Counteracts STAT3 Control of Experimental Inflammatory Arthritis, J. of Immunology, 182:614-622 (2009).
Oganesyan et al., Structural characterization of mutated, ADCC-enhances human Fc fragment, Molecular Immunology, 45:1872-1882 (2008).
Oppmann et al., Alternative assay procedures for cytokines and soluble receptors of the IL-6 family, J. of Immunological Methods, 195:153-159 (1996).

Peipp et al., Molecular Engineering III: Fc Engineering, Handbook of Therapeutic Antibodies, pp. 171-196 (2007).
Pepinsky et al., Improved Pharmacokinetic Properties of Polyethylene Glycol-Modified Form of Interferon-β-1a with Preserved in Vitro Bioactivity, Jr. of Pharmacology and Experimental Therapeutics, 297(3):1059-1066 (2001).
Peters et al., In vivo and in vitro activities of the gp130-Stimulating Designer Cytokine Hyper-IL-6, J. of Immunology, 161:3575-3581 (1998).
Pettit et al., Structure-Function Studies of Interleukin 15 using Site-specific Mutagenesis, Polyethylen Glycol Conjugation, and Homology Modeling, Jr. of Biological Chemistry, 272(4):2312-2318 (1997).
Rabe et al., Transgenic blockade of interleukin 6 transsignaling abrogates inflammation, Blood, 111:1021-1028 (2008).
Rakemann et al., The designer cytokine hyper-interleukin 6 is a potent activator of STAT3-dependent gene transcription in vivo and in vitro, J. Biol. Chem., 274(3):1257-1266 (1999).
Rhodes et al., Identification of MRF4; a new member of the muscle regulatory factor gene family, Genes Dev., 3:2050-2061 (1989).
Rhodes et al., Transformation of Maize by Electroporation of Embryos, Methods in Molecular Biology, 55:121-131 (1995).
Rose-John et al., Studies on the structure and regulation of the human hepatic interleukin-6 receptor, Eur. J. Biochem., 190:79-83 (1990).
Rose-John, S. et al., the IL-6/sIL-6R complex as a novel target for the therapeutic approaches, Expert Opin. Ther. Targets, 11(5): 613-624 (2007).
Sambrook et al., Molecular Cloning: A Laboratory Manual—2nd Edition, Cold Spring Harbor Laboratory Press, pp. I-XXXVIII (1989).
Scharf et al., Heat stress promoters and transcription factors, Results and Problems in Cell Differentiation, 20:125-162 (1994).
Schutt et al., Supplemental Material—Transsignaling of Interleukin-6 Crucially Contributes to Atherosclerosis in Mice, Arterior cler Throm. Biol., 32(2):1-26 (2011).
Schutt et al., Transsignaling of Interleukin-6 Crucially Contributes to Atherosclerosis in Mice, Arterior cler Throm. Vasc. Biol., 32(2):281-290 (2011).
Siam et al., Choosing and using Schzosaccharomyces pombe plasmids, Methods, 33:189-198 (2004).
Sommer, J. et al., Alternative Intronic Polyadenylation Generates the Interleukin-6 Trans-signaling Inhibitor sgp130-E10, Journal of Biological Chemistry, 289(32): 22140-22150 (2014).
Sondermann et al., The 3.2-Å crystal structure of the human IgG1 Fc fragment-FcγRIII complex, Nature, 406:267-273 (2000).
Sprang et al., Cytokine structural taxonomy and mechanisms of receptor engagement, Current Opinion in Structural Biology, 3:815-827 (1993).
Stoger et al., Sowing the seeds of success: pharmaceutical proteins from plants, Current Opinion in Biotechnology, 16:167-173 (2005).
Suzuki et al., CIS3/SOCS3/SSI3 plays a negative regulatory role in STAT3 activation and intestinal inflammation, J. Exp. Med., 193(4):471-481 (2001).
Takamatsu et al., Expression of bacterial chloramphenicol acetyltransferase gene in tobacco plants mediated by TMV-RNA, The EMBO Journal, 6(2):307-311 (1987).
Tanaka et al., Cloning of novel soluble gp130 and detection of its neutralizing autoantibodies in rheumatoid arthritis, J. Clin. Invest., 106:137-144 (2000).
Tang et al., Studies on the PEGylation of Protein at a Specific Site: Sulfhydryl-PEGylation of 97Cys-IFN-gamma, Sheng Wu Hua Xue Yu Sheng Wu Wu Li Xue Bao (Shanghai), 28(3):312-215 (1996) (in Chinese with English abstract).
Tao et al., Studies of Aglycosylated Chimeric Mouse-Human IgG, J. of Immunology, 143(8):2595-2601 (1989).
Tenhumber et al., Characterization of Mutants of the Soluble CP130 Protein in Terms of their binding affinity against the IL6/SIL6R Complex, Cytokine Abstracts, Abstract 152, 39:42 (2007).
Tenhumberg, S. et al., Structure-guided optimization of the interleukin-6 trans-signaling antagonist sgp130, Journal of Biological Chemistry, 283(40): 27200-27207 (2008).

(56) References Cited

OTHER PUBLICATIONS

Tsunoda et al., Selective enhancement of thrombopoetic activity of PEGylated interleukin 6 by a simple procedure using a reversible aminoprotective reagent, Br. J. Haematol., 112:181-188 (2001).
Turkson et al., STAT proteins: novel molecular targets for cancer drug discovery, Oncogene, 19(56):6613-6626 (2000).
UnitProt Interleukin-6 receptor beta chain precursor. HIBI: Interleukin signal transducer, XP002322123 retrieved from EBI Database accession No. P40189 abstract, Feb. 1, 1995 (Feb. 1, 1995).
Utset et al., Modified Anti-CD3 Therapy in Psoriatic Arthritis: A Phase I/II Clinical Trial, J. Rheum., 29:1907-1913 (2002).
Voet et al., Biochemistry, John Wiley and Sons, Inc., pp. 126 and 228-234 (1990).
Vriend et al., What if: A molecular modeling and drug design program, J. Mol. Graphics, 8:52-56 (1990).
Wada et al., Codon usage tabulated from the GenBank genetic sequence data, Nucleic Acids Re., 18(Supplemental):2367-2411 (1990).
Waetzig et al., p38 Mitogen-Activated Protein Kinase Is Activated and Linked to TNF-α Signaling in Inflammatory Bowel Disease, Jr. of Immunology, 168:5342-5351 (2002).
Waetzig, G.H. et al., Hitting a complex target: an update on interleukin-6 trans-signalling, Expert Opinion on Therapeutic Targets 16(2): 225-236 (2012).
Waetzig, G.H. et al., N-linked Glycosylation is essential for the stability but not the signaling function of the interleukin-6 signal transducer glycoprotein 130, Journal of Biological Chemistry, 285(3): 1781-1789 (2010).
Wahl et al., Improved Radioimaging and Tumor Localization with Monoclonal F(ab')2, J. of Nuclear Medicine, 24:316-325 (1983).
Waldmann et al., Metabolism of Immunoglobulins, Progr. Allergy, 13:1-110 (1969).
Ward et al., Influence of Interleukins-6 (IL-6) Dimerization of Formation of the High Affinity Hexameric IL-6 Receptor Complex, J. of Bio. Chem., 271(33):20138-20144 (1996).
Wells et al., Perspectives in Biochemistry: Additivity of Mutational Effects in Proteins, Biochem., 29(37):8509-8517 (1990).
Wigler et al., Transfer of Purified Herpes Virus Thymidine Kinase Gene to Cultured Mouse Cells, Cell 11:223-232 (1977).
Wigler et al., Transformation of mammalian cells with an amplifiable dominant-acting gene, Proc. Natl. Acad. Sci., 77(6):3567-3570 (1980).
Wildt et al., The Humanization of N-Glycosylation Pathways in Yeast, Nature Reviews, 3:119-128 (2005).
Wines et al., the IgG Fc Contains Distinc Fc Receptor (FcR) Binding Sites: The Leukocyte Receptors FcγRIIIa Bind to a Region in the Fc Distinct from that Recognized by Neonatal FcR and Protein A1, Jr. of Immunology, 164:5313-5318 (2000).
Winter et al., The Expression of Heat Shock Protein and Cognate Genes During Plant Development, Results and Problems in Cell Differentiation, pp. 85-105 (1991).
Woodle et al., Phase I Trial of Humanized, Fc Receptor nonbinding OKT3 Antibody huOKT3γ1(Ala-Ala) in the treatment of acute renal allograft rejection, Transplantation, 68(5):608-616 (1999).
Wright et al., Effect of glycosylation on antibody function: implications for genetic engineering, TibTech., 15:28-32 (1997).
Written Opinion for PCT/IB2015/002459, 5 pages (dated May 11, 2016).
Written Opinion for PCT/NL2015/050837, 7 pages (dated Jun. 2, 2016).
Yoshizaki et al., Interleukin-6 in autoimmune disorders, Semin. Immunol., 4:155-166 (1992).
Youngster et al., Structure Biology and Therapeutic Implications of Pegylated Interferon Alpha-2b, Current Pharmaceutical Design, 8:2139-2157 (2002).
O'Brien, J. J. et al, Use of Azathioprine or 6-Mercaptopurine in the Treatment of Crohn's Disease, Gastroenterology, 101(1): 39-46 (1991).

* cited by examiner

```
2161  cctcaggtgtacacactgcctccatctagggcaggagatgaccaagaatcaggtgtccctgacctgtctgtgaagggcttctacccttct
721    ·P··Q··V··Y··T··L··P··P··S··R··E··E··M··T··K··N··Q··V··S··L··T··C··L··V··K··G··F··Y··P··S·

2251  gatatcgctgtggagtggcagtctaatggccagcccgagaacaattacaagaccacacccctgtgctggatctgacggctcctcttc
751    ·D··I··A··V··E··W··E··S··N··G··Q··P··E··N··N··Y··K··T··T··P··P··V··L··D··S··D··G··S··F··F·

2341  ctgtactccaaactgaccgtggacaagtctagatggcagcagggcaacgtgttctcttgttccgtgatgcacgagctctgcacaatcac
781    ·L··Y··S··K··L··T··V··D··K··S··R··W··Q··Q··G··N··V··F··S··C··S··V··M··H··E··A··L··H··N··H·

2431  tataccccagaagtccctgtctctgtcctggcaag
811    ·Y··T··Q··K··S··L··S··L··S··P··G··K·
```

FIG. 3 Continued

Fragment: CMV IE Promoter
Source: Cytomegalovirus
Plasmid Location: 37-620
Function: Mammalian expression promoter
Sequence:
ATTAATAGTAATCAATTACGGGGTCATTAGTTCATAGCCCATATATGGAGTTCCGCGTTACATAACT
TACGGTAAATGGCCCGCCTGGCTGACCGCCCAACGACCCCCGCCCATTGACGTCAATAATGACGTA
TGTTCCCATAGTAACGCCAATAGGGACTTTCCATTGACGTCAATGGGTGGAGTATTTACGGTAAAC
TGCCCACTTGGCAGTACATCAAGTGTATCATATGCCAAGTACGCCCCCTATTGACGTCAATGACGG
TAAATGGCCCGCCTGGCATTATGCCCAGTACATGACCTTATGGGACTTTCCTACTTGGCAGTACATC
TACGTATTAGTCATCGCTATTACCATGGTGATGCGGTTTTGGCAGTACATCAATGGGCGTGGATAG
CGGTTTGACTCACGGGGATTTCCAAGTCTCCACCCCATTGACGTCAATGGGAGTTTGTTTTGGCACC
AAAATCAACGGGACTTTCCAAAATGTCGTAACAACTCCGCCCCATTGACGCAAATGGGCGGTAGGC
GTGTACGGTGGGAGGTCTATATAAGCAGAGCTCGTTTAGTGAACCGTCAGATC

FIG. 6A

Fragment: Human IgH Poly A
Source: Human
Plasmid Location: 3211-3537
Function: Polyadenylation sequence
Sequence:
GTGCCACGGCCGGCAAGCCCCCGCTCCCCGGGCTCTCGCGGTCGCACGAGGATGCTTGGCACGTAC
CCCGTCTACATACTTCCCAGGCACCCAGCATGGAAATAAAGCACCCACCACTGCCCTGGGCCCCTG
CGAGACTGTGATGGTTCTTTCCACGGGTCAGGCCGAGTCTGAGGCCTGAGTGGCATGAGGGAGGCA
GAGTGGGTCCCACTGTCCCCACACTGGCCCAGGCTGTGCAGGTGTGCCTGGGCCGCCTAGGGTGGG
GCTCAGCCAGGGGCTGCCCTCGGCAGGGTGGGGGATTTGCCAGCGTGGCCCTCCCTCCAGCAG

FIG. 6B

Fragment: Amp (bla) gene
Source: Originally sourced from Salmonella paratyphi
Plasmid Location: 4362-5222 (complementary strand)
Function: Bacterial resistance
Sequence:
TTACCAATGCTTAATCAGTGAGGCACCTATCTCAGCGATCTGTCTATTTCGTTCATCCATAGTTGCC
TGACTCCCCGTCGTGTAGATAACTACGATACGGGAGGGCTTACCATCTGGCCCCAGTGCTGCAATG
ATACCGCGAGACCCACGCTCACCGGCTCCAGATTTATCAGCAATAAACCAGCCAGCCGGAAGGGC
CGAGCGCAGAAGTGGTCCTGCAACTTTATCCGCCTCCATCCAGTCTATTAATTGTTGCCGGGAAGCT
AGAGTAAGTAGTTCGCCAGTTAATAGTTTGCGCAACGTTGTTGCCATTGCTACAGGCATCGTGGTG
TCACGCTCGTCGTTTGGTATGGCTTCATTCAGCTCCGGTTCCCAACGATCAAGGCGAGTTACATGAT
CCCCCATGTTGTGCAAAAAAGCGGTTAGCTCCTTCGGTCCTCCGATCGTTGTCAGAAGTAAGTTGG
CCGCAGTGTTATCACTCATGGTTATGGCAGCACTGCATAATTCTCTTACTGTCATGCCATCCGTAAG
ATGCTTTTCTGTGACTGGTGAGTACTCAACCAAGTCATTCTGAGAATAGTGTATGCGGCGACCGAG
TTGCTCTTGCCCGGCGTCAATACGGGATAATACCGCGCCACATAGCAGAACTTTAAAAGTGCTCAT
CATTGGAAAACGTTCTTCGGGGCGAAAACTCTCAAGGATCTTACCGCTGTTGAGATCCAGTTCGAT
GTAACCCACTCGTGCACCCAACTGATCTTCAGCATCTTTTACTTTCACCAGCGTTTCTGGGTGAGCA
AAAACAGGAAGGCAAAATGCCGCAAAAAAGGGAATAAGGGCGACACGGAAATGTTGAATACTCA
T

FIG. 6C

Fragment: SV40 Promoter
Source: Simian Virus 40
Plasmid Location: 5406-5761
Function: Mammalian expression promoter
Sequence:
CACGAGGCCCTATTGATTATTGACTAGCTAGTGTGGAATGTGTGTCAGTTAGGGTGTGGAAAGTCC
CCAGGCTCCCCAGCAGGCAGAAGTATGCAAAGCATGCATCTCAATTAGTCAGCAACCAGGTGTGG
AAAGTCCCCAGGCTCCCCAGCAGGCAGAAGTATGCAAAGCATGCATCTCAATTAGTCAGCAACCAT
AGTCCCGCCCCTAACTCCGCCCATCCCGCCCCTAACTCCGCCCAGTTCCGCCCATTCTCCGCCCAT
GGCTGACTAATTTTTTTTATTTATGCAGAGGCCGAGGCCGCCTCGGCCTCTGAGCTATTCCAGAAGT
AGTGAGGAGGCTTTTTTGGAGGCCT

FIG. 6D

Fragment: Dihydrofolate Reductase Coding Sequence
Source: Cytomegalovirus
Plasmid Location: 5794-6357
Function: Selection in CHO dhfr- cells
Sequence:
ATGGTTCGACCATTGAACTGCATCGTCGCCGTGTCCCAAAATATGGGGATTGGCAAGAACGGAGAC
CGACCCTGGCCTCCGCTCAGGAACGAGTTCAAGTACTTCCAAAGAATGACCACAACCTCTTCAGTG
GAAGGTAAACAGAATCTGGTGATTATGGGTAGGAAAACCTGGTTCTCCATTCCTGAGAAGAATCGA
CCTTTAAAGGACAGAATTAATATAGTTCTCAGTAGAGAACTCAAAGAACCACCACGAGGAGCTCAT
TTTCTTGCCAAAAGTTTGGATGATGCCTTAAGACTTATTGAACAACCGGAATTGGCAAGTAAAGTA
GACATGGTTTGGATAGTCGGAGGCAGTTCTGTTTACCAGGAAGCCATGAATCAACCAGGCCACCTC
AGACTCTTTGTGACAAGGATCATGCAGGAATTTGAAAGTGACACGTTTTTCCCAGAAATTGATTTG
GGGAAATATAAACTTCTCCCAGAATACCCAGGCGTCCTCTCTGAGGTCCAGGAGGAAAAAGGCAT
CAAGTATAAGTTTGAAGTCTACGAGAAGAAAGACTAA

FIG. 6E

Fragment: SV40 Poly
Source: Simian Virus 40
Plasmid Location: 6358-6680
Function: Polyadenylation sequence
Sequence:
CAGGAAGATGCTTTCAAGTTCTCTGCTCCCCTCCTAAAGCTATGCATTTTTATAAGACCATGGGACT
TTTGCTGGCTTTAGATCATAATCAGCCATACCACATTTGTAGAGGTTTTACTTGCTTTAAAAAACCT
CCCACACCTCCCCCTGAACCTGAAACATAAAATGAATGCAATTGTTGTTGTTAACTTGTTTATTGCA
GCTTCTAATGGTTACAAATAAAGCAATAGCATCACAAATTTCACAAATAAAGCATTTTTTTCACTGC
ATTCTAGTTGTGGTTTGTCCAAACTCATCAATGTATCTTATCATGTCTGGATCGG

```
 421                                         · W · T · I · P · R · E · S · V · K · K · Y · I · L · E · W · C · V · L · S · D · K · A · P · C · I · T · D · W · Q · Q ·
1351   gaggatgcaccgtgcatagaacctacctggccgattctggccaatctgctatctgatctactaccgtgaccctgaccgtgtatgctgat
 451    · E · D · G · T · V · H · R · T · Y · L · R · G · N · L · A · E · S · K · C · Y · L · I · T · V · T · P · V · Y · A · D ·
1441   ggacctggctctcctgagtctcaaggcctacctgaaggcaggctcctccatctaaggacctgaggacgtgaggacaaagaaggtgggcaag
 481    · G · P · G · S · P · E · S · I · K · A · Y · L · K · Q · A · P · S · K · D · P · T · V · R · T · K · K · V · G · K ·
1531   aacgaggctgctgctgatgtcagctgggatggatcagttgtgctgtgcagaacgctcatccggaactacaccatcttctaccgaccatcatc
 511    · N · E · A · V · L · E · W · D · Q · L · P · V · Q · N · G · F · I · R · N · Y · T · I · F · Y · R · T · I · I ·
1621   ggcaatgagacgccgtgaactgttcccaccacactgtaccacctgtcctctgacacctgtacatgtgagaatg
 541    · G · N · E · T · A · V · N · V · D · S · S · H · T · E · Y · T · L · S · L · T · S · D · T · L · Y · M · V · R · M ·
1711   gccgcttataccgatgagggcggcaaggatggcaagcctgagttcaccttcacccaccacccctaagttcgccagggcgaggacaagaccaccacc
 571    · A · A · Y · T · D · E · G · G · K · D · G · P · E · F · T · F · T · P · K · F · A · Q · E · D · K · T · H · T ·
1801   tgtcctcctgtgtcctgctcctgaggggcctcccctgaggtctctgtgttctgttctgttccccaaagccaaggataccctgatgatctccaga
 601    · C · P · P · C · P · A · E · G · A · P · S · V · F · L · F · P · P · K · P · K · D · T · L · M · I · S · R ·
1891   accctgagtgcacatgttggtggatgtctcatgaggacccgaggtgaagttcaactggtacgtggatggcgtggaggtgcac
 631    · T · P · E · V · T · C · V · V · V · D · V · S · H · E · D · P · E · V · K · F · N · W · Y · V · D · G · V · E · V · H ·
1981   aatgctaagaccaagccctaggaggagcagtacaactccacctacagagtggtgtctgtgctgacagtggtgctgcatcaggattggctgaac
 661    · N · A · K · T · K · P · R · E · E · Q · Y · N · S · T · Y · R · V · V · S · V · L · T · V · L · H · Q · D · W · L · N ·
2071   ggcaaggagtacaagtgcaaggtctccaacaaggccctgcctgccctatcgaaaagaccatctccaaggctaaggaacagccccagagag
 691    · G · K · E · Y · K · C · K · V · S · N · K · A · L · P · A · P · I · E · K · T · I · S · K · A · K · G · Q · P · R · E ·
2161   cctcaggtgtacacactgcctccatctagggaggagatgaccaagaatcaggtgtcctgacctgtctggtgaagggcttctacccctcct
 721    · P · Q · V · Y · T · L · P · P · S · R · E · E · M · T · K · N · Q · V · S · L · T · C · L · V · K · G · F · Y · P · S ·
2251   gatatcgctgtgagtggagttctaatggccagcccagaacaattacaagaccaccccttcttcctgtgctggattctgacggctcctcttc
 751    · D · I · A · V · E · W · E · S · N · G · Q · P · E · N · N · Y · K · T · T · P · P · V · L · D · S · D · G · S · F · F ·
2341   ctgtactccaaactgaccgtggacaagtctagatggcagcaggcaacgtgttctttgtcctgatgcacgagagcctctgcacaatcac
 781    · L · Y · S · K · L · T · V · D · K · S · R · W · Q · Q · G · N · V · F · S · C · S · V · M · H · E · A · L · H · N · H ·
2431   tataccagaagaagtccctgtctcctgcaag
 811    · Y · T · Q · K · S · L · S · L · S · P · G · K ·
```

FIG. 7 Continued

SELECTIVE IL-6-TRANS-SIGNALLING INHIBITOR COMPOSITIONS

CROSS REFERENCE TO RELATED APPLICATIONS

This application is the National Stage of International Application No. PCT/NL2015/050837, filed Dec. 1, 2015 which claims the benefit of European Application No. EP14195726.6, filed Dec. 1, 2014, the contents of each of which are hereby incorporated herein by reference in their entirety.

SEQUENCE LISTING

In accordance with 37 CFR § 1.52(e)(5), a Sequence Listing in the form of a text file (entitled "2010786-0017 SL.txt", created on Apr. 9, 2019 and having a size of 58,312 bytes) is hereby incorporated by reference in its entirety.

BACKGROUND

IL-6 is a pleiotropic cytokine produced by hematopoietic and non-hematopoietic cells, e.g. in response to infection and tissue damage. IL-6 exerts its multiple biological activities through two main signalling pathways, a so-called classic ligand-receptor pathway via membrane-bound IL-6R present mainly on hepatocytes and certain leukocytes, and a trans-signalling pathway via circulating sIL-6R originating from proteolytic cleavage of the membrane-bound IL-6R or from alternative splicing.

In the classic pathway, IL-6 directly binds to membrane-bound IL-6R on the surface of a limited range of cell types. The IL-6/IL-6R complex associates with a pre-formed dimer of the signal-transducing gp130 receptor protein, causing steric changes in the gp130 homodimer and thereby initiating an intracellular signalling cascade. Classic signalling is responsible for acute inflammatory defense mechanisms and crucial physiological IL-6 functions, such as growth and regenerative signals for intestinal epithelial cells.

The extracellular domains of IL-6R and gp130 can be generated without the membrane-anchoring domains by translation of alternatively-spliced mRNAs resulting in sIL-6R and sgp130 variants. Additionally, the extracellular domain of IL-6R can be shed by membrane-bound proteases of the A disintegrin and metalloprotease (ADAM) family (in humans, ADAM17) to generate sIL-6R. In the trans-signalling process, sIL-6R binds to IL-6, forming an agonistic complex which binds to trans-membrane gp130 dimers present on a multitude of cell types that do not express membrane-bound IL-6R; IL-6 signalling by signal transducers and activators of transcription (STATS) is then induced in cells which do not normally respond to IL-6. The activity of the IL-6/sIL-6R complex is normally controlled by high levels of sgp130 present in the circulation which effectively compete with membrane-bound gp130. Trans-signalling is mainly involved in chronic inflammation and has been shown to prevent disease-promoting mucosal T-cell populations from going into apoptosis.

It would be desirable to have a molecule that mimics the natural trans-signalling inhibitor sgp130, but with a higher binding affinity and, consequently, a stronger inhibitory activity. Moreover, it would be desirable to have a molecule that can be administered to humans with minimal toxicity and immunogenic potential.

SUMMARY OF THE INVENTION

It has now been found that a selective IL-6-trans-signalling inhibitor can be administered to humans without any significant deleterious effects over a large dosage range. This inhibitor is substantially free of aggregation and glycosylation patterns that are associated with immunogenic potential. In addition, the inhibitor provides a favorable half-life in humans.

The invention provides a polypeptide dimer comprising two monomers of SEQ ID NO: 1. Preferably the monomers are linked by one or more disulfide bridges. Preferably, dimer is linked by disulfide bridges at positions $Cys_{623}$ and $Cys_{626}$ of SEQ ID NO: 1. The invention also provides a polypeptide dimer comprising two monomers of SEQ ID NO: 2. Preferably the monomers are linked by one or more disulfide bridges. Preferably, the dimer is linked by disulfide bridges at positions $Cys_{623}$ and $Cys_{626}$ of SEQ ID NO: 2.

Preferably, the polypeptide dimer comprises no greater than 6% of galactose-alpha-1,3-galactose per mole polypeptide and/or includes at least 52% of glycans having one or more sialic acid residues.

The invention also provides a composition comprising the polypeptide dimers disclosed herein. Preferably, no greater than 5% of the polypeptide dimer in the composition is present as an oligomeric aggregate and/or the composition comprises no greater than 10.0%, 8.0%, 6.0 or 4.0% by weight of polypeptides that are a truncated variation of the polypeptide (e.g., a truncated version of SEQ ID NO: 1 with respect to polypeptides of SEQ ID NO: 1 or a truncated version of SEQ ID NO: 2 with respect to polypeptides of SEQ ID NO: 2). Moreover, the dimers in such compositions can include the features described in the paragraph above and described in further detail below.

The invention further includes methods of treating conditions described herein with a polypeptide dimer or composition described herein. In addition, the invention includes the use of polypeptide dimers and compositions described herein for the manufacture of a medicament for treating a condition described herein.

In addition, the invention includes methods of preparing the polypeptide dimers, which encompasses associated nucleotide sequences, expression vectors, cells expressing the polypeptide, and purifying the polypeptide. In particular, the invention includes nucleotide sequences encoding the polypeptides disclosed herein, in particular, a polypeptide of SEQ ID NO: 1 or SEQ ID NO:2 or a polypeptide having an amino acid sequence at least 90% identical to SEQ ID NO: 1 or SEQ ID NO:2. Preferably, the nucleotide sequence is at least 90% identical to the nucleotide sequence of FIG. 3 or FIG. 7 and more preferably encodes a polypeptide of SEQ ID NO: 1 or SEQ ID NO: 2. Preferably the nucleotide sequence is the nucleotide sequence of FIG. 7.

BRIEF DESCRIPTION OF THE DRAWINGS

FIG. 3 shows the nucleotide and amino acid sequence (SEQ ID NO: 6 and SEQ ID NO: 1, respectively) of the single gp130-Fc subunit.

FIGS. 6A-6F show nucleotide sequence elements of the expression plasmid pFER02. FIG. 6A depicts CMV IE Promoter (SEQ ID NO: 8). FIG. 6B depicts Human IgH PolyA (SEQ ID NO: 9). FIG. 6C depicts Amp (bla) gene (SEQ ID NO: 10). FIG. 6D depicts SV40 Promoter (SEQ ID NO: 11). FIG. 6E depicts Dihydrofolate Reductase Coding Sequence (SEQ ID NO: 12). FIG. 6F depicts SV40 Poly (SEQ ID NO: 13).

FIG. 7 shows the amino acid sequence of the single gp130-Fc subunit (SEQ ID NO: 15) and the nucleotide sequence optimized for optimal codon usage in CHO cells (SEQ ID NO: 14).

DETAILED DESCRIPTION OF THE INVENTION

Figure 2:
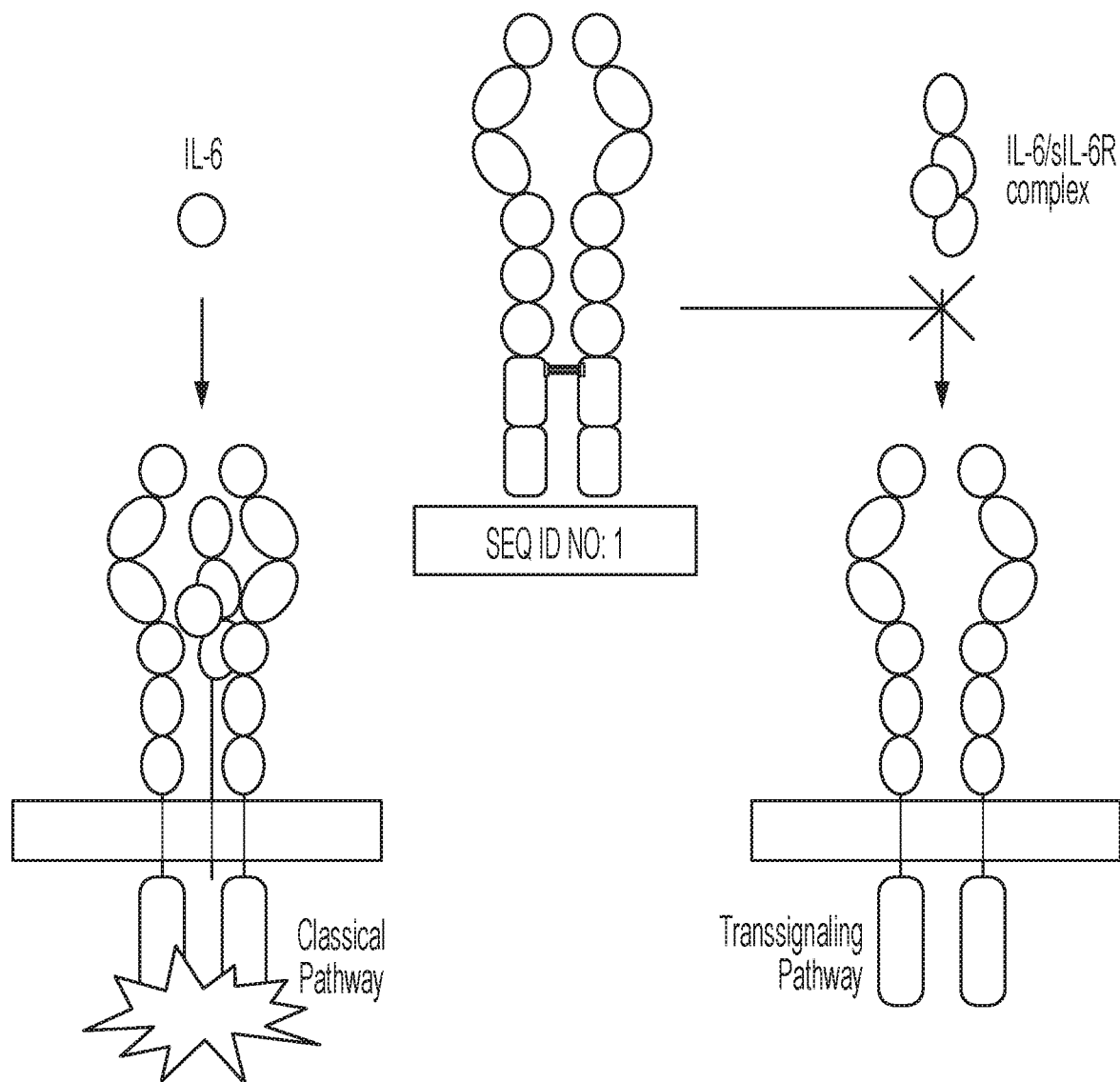
FIG. 2 shows that a polypeptide dimer comprising two monomers of SEQ ID NO: 1 does not interfere with IL-6 binding to membrane-bound IL-6R (classic signalling), but selectively binds to the IL-6/sIL-6R complex and prevents trans-signalling.

One aspect of the invention provides a dimer of two gp130-Fc fusion monomers (e.g., two monomers of SEQ ID NO:1). In its active form, the polypeptide of SEQ ID NO: 1 exists as a dimer linked by two disulfide linkages at $Cys_{623}$ and $Cys_{626}$ (FIG. 2). SEQ ID NO: 2 corresponds to the amino acid sequence of a gp130-Fc fusion monomer having the endogenous signal peptide. The signal peptide is removed during protein synthesis, resulting in the production of the polypeptide of SEQ ID NO: 1.

Figure 1:
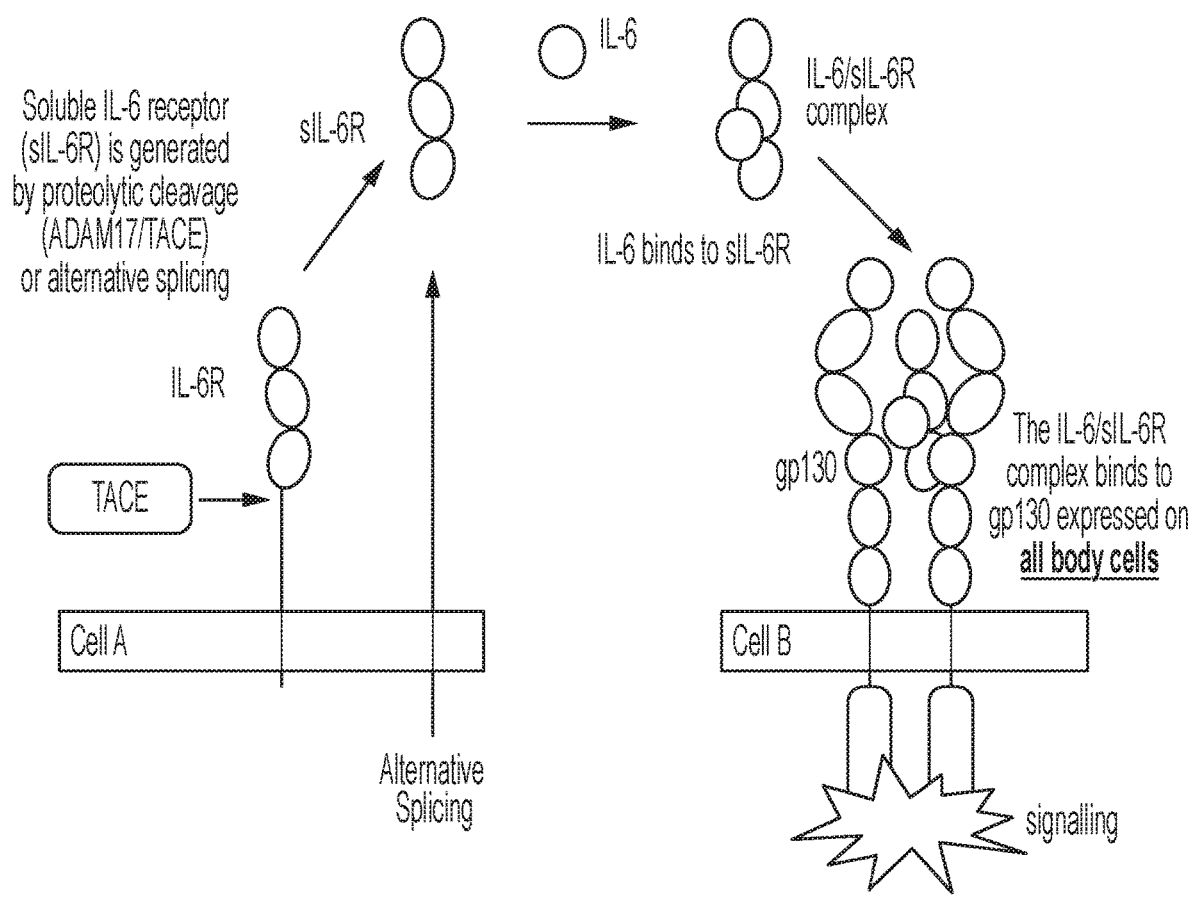
FIG. 1 shows the trans-signalling pathway of IL-6. sIL-6R generated from alternatively spliced mRNA or proteolytic cleavage is able to bind to IL-6 to form a IL-6/sIL-6 complex that binds to gp130 present on the vast majority of body cell types and induce a intracellular signalling cascade.

The polypeptide dimers described herein selectively inhibit excessive trans-signalling (FIG. 1) and induces apoptosis of the detrimental T-cells involved in multiple inflammatory diseases. The polypeptide dimer targets and neutralizes IL-6/sIL-6R complexes and is therefore expected to only inhibit IL-6 trans-signalling in the desired therapeutic concentrations, leaving classic signalling and its many physiological functions, as well as its acute inflammatory defense mechanisms, intact (FIG. 2). The polypeptide dimer is believed to be unable to interfere with classic IL-6 signalling due to steric hindrance; the Fc portion is unable to insert into a cell membrane, making the gp130 portion unavailable for binding to membrane-bound IL-6/sIL-6R complex. Thus, the polypeptide is expected to have efficacy similar to global IL-6 blockade (e.g., tocilizumab, sirukumab) but with fewer side effects.

Polypeptide dimers described herein preferably comprise gp130-Fc monomers having the sequence corresponding to SEQ ID NO:1. In certain embodiments, the monomers have the sequence corresponding to SEQ ID NO:2. In certain embodiments, polypeptide dimers described herein comprise polypeptides having at least 90%, 95%, 97%, 98%, 99% or 99.5% sequence identity to SEQ ID NO: 1 or SEQ ID NO:2. Preferably, the polypeptide comprises the gp130 D6 domain (in particular amino acids TFTTPKFAQGE: amino acid positions 585-595 of SEQ ID NO:1), AEGA in the Fc domain hinge region (amino acid positions 609-612 of SEQ ID NO:1) and does not comprise a linker between the gp130 portion and the Fc domain. In a preferred embodiment, the disclosure provides a polypeptide dimer comprising two monomers having an amino acid sequence at least 90% sequence identify to SEQ ID NO: 1, wherein the amino acid sequence comprises the gp130 D6 domain, AEGA in the Fc domain hinge region, and there is no linker present between the gp130 portion and the Fc domain. In a preferred embodiment, the disclosure provides a polypeptide dimer comprising two monomers having an amino acid sequence at least 90% sequence identify to SEQ ID NO: 2, wherein the amino acid sequence comprises the gp130 D6 domain, AEGA in the Fc domain hinge region, and there is no linker present between the gp130 portion and the Fc domain, preferably wherein the monomers are linked by one or more disulfide bridges, and more preferably wherein:
  a. the polypeptide dimer comprises no greater than 6% of galactose-alpha-1,3-galactose per mole polypeptide, preferably no greater than 3 mol %, more preferably no greater than 1 mol %, even more preferably no greater than 0.5 mol % of galactose-alpha-1,3-galactose,
  b. the polypeptide dimer comprises glycans, wherein a mean of at least 52%, preferably at least 54% of the glycans include one or more sialic acid residues, more preferably 52-65% or
  c. both.

It is desirable for polypeptides to be substantially free of galactose-alpha-1,3-galactose moieties, as these are associated with an immunogenic response. It was surprisingly found that dimers of the invention have low levels of such moieties. In preferred embodiments, the polypeptide (e.g., a polypeptide monomer and/or dimer described herein) contains no greater than 6% of galactose-alpha-1,3-galactose per mole polypeptide. Preferably, the polypeptide contains no greater than 4 mole %, 3 mole %, 2 mole %, 1 mole %, 0.5 mole %, 0.2 mole %, 0.1 mole % or even an undetectable level of galactose-alpha-1,3-galactose (e.g., as measured by WAX-HPLC, NP-HPLC or WAX, preferably as determined by WAX-HPLC). In other embodiments, the polypeptides contain less than 6%, 4%, 3%, 2%, 1%, 0.5%, 0.2%, or even 0.1% of galactose-alpha-1,3-galactose, relative to the total amount of glycans, either by mass or on a molar basis.

In some embodiments, it is also desirable for a polypeptide of the invention to be sialylated, e.g., to increase the half-life of polypeptides of the invention. Each chain of the polypeptide contains 10 putative N-glycosylation sites; nine N-glycosylation sites are located in the gp130 portion and one N-glycosylation site is located in the Fc portion. The polypeptide therefore contains a total of 20 glycosylation sites. In certain embodiments, a mean of at least 52% or at least 54% of glycans on the polypeptide include a sialic acid residue, such as a mean from 52-65% (e.g., as measured by WAX-HPLC, NP-HPLC or WAX, preferably as determined by WAX-HPLC). Preferably, the polypeptide of the invention has an approximate molecular weight of 220 kDa; each 93 kDA having an additional ~20 kDa molecular weight derived from 10 N-glycosylation chains.

In some embodiments, the invention provides compositions comprising a plurality of polypeptides described herein (e.g., a plurality of polypeptide monomers and/or polypeptide dimers described herein). In some embodiments, a composition comprises a mean of at least 25% (e.g., at least 26%, 27%, 28%, 29%, 30%, 31%, 32%, 33%, 34%, 35%, 36%, 37%, 38%, 39%, or 40%) mono-sialylated polypeptides; a mean of at least 10% (e.g., at least 11%, 12%, 13%, 14%, 15%, 16%, 17%, 18%, 19%, 20%, 21%, 22%, 23%, 24%, or 25%) di-sialylated polypeptides; a mean of at least 1% (e.g., at least 1%, 1.5%, 2%, 2.5%, 3%, 3.5%, 4%, 4.5%, 5%, 5.5%, or 6%) tri-sialylated polypeptides; and/or a mean of at least 0.1% (e.g., at least 0.2%, 0.3%, 0.4%, 0.5%, 0.6%, 0.7%, 0.8%, 0.9%, or 1%) tetra-sialylated glycans; relative to glycan groups in the composition.

It is further desirable to minimize the extent to which polypeptides aggregate, which is herein referred to as oligomerization which results in oligomeric aggregates. "Oligomeric aggregates" as used herein, does not refer to the active dimerized peptide. Instead, the term refers to at an aggregate of a least three monomers (e.g., of SEQ ID NO: 1) or, more typically, at least a dimer of active dimers. It was surprisingly found that the peptide dimers of the invention display low levels of aggregation. In certain embodiments, less than 5%, less than 4%, less than 3%, less than 2%, less than 1.5%, or even less than 1.0% of the polypeptide is present as an oligomer. The oligomer content can be measured, for example, by size exclusion chromatography-multi angle light scatting (SEC-MALS) or SEC-UV.

Preferably, the polypeptide is present in its full-length form (e.g., includes two full length monomers, e.g., of SEQ ID NO:1). However, cell culture can produce a truncated variant referred to herein as the single gp130 form (SGF). SGF is a covalently-bound two-chain molecule, one chain comprising a the full-length gp130-Fc monomer (e.g., of SEQ ID NO:1) and a second chain comprising a truncated gp130-Fc monomer (e.g., a truncation of SEQ ID NO: 1), which second chain includes the Fc domain and lacks most or all of the gp130 domain (e.g., terminated before the linker sequence to the Fc region). Studies to date demonstrate that SGF does not have a heterogeneous amino-terminus. SGF can be formed at consistent levels in a bioreactor and once formed, SGF levels are not readily changed during purification, processing or accelerated storage conditions. SGF levels are difficult to remove during purification due to similar physical-chemical properties to the full-length form of the polypeptide dimer; thus efforts to remove SGF can result in a significant reduction in yield. It was surprisingly found that dimers of the invention are nearly always full-length. In certain embodiments, the composition of the invention comprises no greater than 4.0% by weight, 3.0% by weight, 2.0% by weight or even 1.5% by weight of polypeptides that are a truncated variation of the polypeptide of SEQ ID NO: 1 with respect to polypeptides of SEQ ID NO: 1. In certain embodiments, the composition of the invention comprises no greater than 4.0% by weight, 3.0% by weight, 2.0% by weight or even 1.5% by weight of polypeptides that are a truncated variation of the polypeptide of SEQ ID NO: 2 with respect to polypeptides of SEQ ID NO: 2.

The polypeptide of the invention is typically administered parenterally, such as intravenously or subcutaneously.

Suitable formulations include those comprising a surfactant, particularly a nonionic surfactant such as a polysorbate surfactant (e.g., polysorbate 20). Formulations can also include buffering agents and sugars. An exemplary buffering agent is histidine. An exemplary sugar is sucrose. Thus, a suitable formulation could include polysorbate 20 (e.g., 0.01-1 mg/mL, 0.02-0.5 mg/mL, 0.05-0.2 mg/mL), histidine (e.g., 0.5 mM-250 mM, 1-100 mM, 5-50 mM, 10-20 mM) and sucrose (e.g., 10-1000 mM, 20-500 mM, 100-300 mM, 150-250 mM).

Indications

In acute inflammation, IL-6 has been shown to induce the acute phase response in the liver leading to release of the cascade of acute phase proteins, in particular CRP. By forming a complex with sIL-6R shed by apoptotic neutrophils at the site of inflammation and binding of the resulting IL-6/sIL-6R trans-signalling complex to the signal transducer gp130 on endothelial cells, IL-6 induces expression of chemokines such as monocyte chemotactic protein (MCP)-1 and attracts mononuclear cells. This leads to the resolution of acute inflammation and to the initiation of an adaptive immune response. Thus, in acute inflammation, IL-6 with sIL-6R complex supports the transition between the early predominantly neutrophilic stage of inflammation and the more sustained mononuclear cell influx ultimately also leading to the resolution of inflammation.

Chronic inflammation, such as in Crohn's disease (CD), ulcerative colitis (UC), rheumatoid arthritis (RA) or psoriasis, is histologically associated with the presence of mononuclear cells, such as macrophages and lymphocytes, persisting in the tissue after having been acquired for the resolution of the acute inflammatory phase. In models of chronic inflammatory diseases, IL-6 seems to have a detrimental role favouring mononuclear-cell accumulation at the site of injury, through induction of continuous MCP-1 secretion, angio-proliferation and anti-apoptotic functions on T-cells.

Inflammatory bowel disease (IBD), namely CD or UC, is a chronic inflammation occurring in the gut of susceptible individuals that is believed to be independent of a specific pathogen. Alterations in the epithelial mucosal barrier with increased intestinal permeability lead to an enhanced exposure of the mucosal immune system to luminal antigens, which causes an inappropriate activation of the intestinal immune system in patients. The uncontrolled activation of mucosal CD4+ T-lymphocytes with the consecutive excessive release of proinflammatory cytokines induces pathogenic gastrointestinal inflammation and tissue damage. There is a consensus that the main activated immune cells involved in the pathogenesis of IBD are intestinal T-cells and macrophages.

IL-6 is shown to be a central cytokine in IBD in humans. Patients with CD and UC have been found to produce increased levels of IL-6 when compared with controls, the IL-6 levels being correlated to clinical activity. CD patients have also been found to have increased levels of sIL-6R and consequently, IL-6/sIL-6R complex in serum. Lamina propria mononuclear cells obtained from surgical colon specimens from patients with CD and UC showed that both CD4+ T-cells and macrophages produced increased amounts of IL-6 compared to controls. sIL-6R was found to be released via shedding from the surface of macrophages and mononuclear cells with increased production associated with elevated levels of IL-6. In patients with CD, mucosal T-cells showed strong evidence for IL-6 trans-signalling with activation of STATS, bcl-2 and bcl-x1. The blockade of IL-6 trans-signalling caused T-cell apoptosis, indicating that the IL-6/sIL-6R system mediates the resistance of T-cells to apoptosis in CD.

Thus, in IBD patients, acquired accumulation of disease-promoting CD4+ T-cells in the lamina propria leading to perpetuation of inflammation is critically dependent on anti-apoptotic IL-6/sIL-6R trans-signalling. It is believed that by acting on the IL-6/sIL-6R complex, the polypeptide disclosed herein is useful in treating CD and other inflammatory diseases.

Thus, the polypeptide of the invention can treat IL-6-mediated conditions. IL-6-mediated conditions include inflammatory disease or a cancer. In this regard, the polypeptides and compositions described herein may be administered to a subject having an inflammatory disease, such as juvenile idiopathic arthritis, Crohn's disease, colitis (e.g., colitis not associated with IBD, including radiation colitis, diverticular colitis, ischemic colitis, infectious colitis, celiac disease, autoimmune colitis, or colitis resulting from allergies affecting the colon), dermatitis, psoriasis, uveitis, diverticulitis, hepatitis, irritable bowel syndrome (IBS), lupus erythematous, nephritis, Parkinson's disease, ulcerative colitis, multiple sclerosis (MS), Alzheimer's disease, arthritis, rheumatoid arthritis, asthma, and various cardiovascular diseases such as atherosclerosis and vasculitis. In certain embodiments, the inflammatory disease is selected from the group consisting of, diabetes, gout, cryopyrin-associated periodic syndrome, and chronic obstructive pulmonary disorder.

Preferably, the inflammatory disease or IL-6-mediated condition is inflammatory bowel disease, preferably wherein the treatment induces the remission of inflammatory bowel disease. Preferably, the inflammatory bowel disease is Crohn's disease or ulcerative colitis, preferably wherein the treatment maintains the remission of inflammatory bowel disease. Preferably, the inflammatory disease or IL-6-mediated condition is rheumatoid arthritis, psoriasis, uveitis or atherosclerosis. Preferably, the inflammatory disease or IL-6-mediated condition is colitis not associated with inflammatory bowel disease, preferably wherein the colitis is radiation colitis, diverticular colitis, ischemic colitis, infectious colitis, celiac disease, autoimmune colitis, or colitis resulting from allergies affecting the colon. Preferably, the inflammatory disease or IL-6-mediated condition is selected from Crohn's disease, ulcerative colitis, rheumatoid arthritis and psoriasis, more preferably from Crohn's disease and ulcerative colitis.

For inflammatory disease such as inflammatory bowel disease, treatment can include remission of the condition, maintenance of remission of the condition, or both.

Other embodiments provide a method of treating, reducing the severity of or preventing a cancer, including, but not limited to multiple myeloma, plasma cell leukemia, renal cell carcinoma, Kaposi's sarcoma, colorectal cancer, gastric cancer, melanoma, leukemia, lymphoma, glioma, glioblastoma multiforme, lung cancer (including but not limited to non-small cell lung cancer (NSCLC; both adenocarcinoma and squamous cell carcinoma)), non-Hodgkin's lymphoma, Hodgkin's disease, plasmocytoma, sarcoma, thymoma, breast cancer, prostate cancer, hepatocellular carcinoma, bladder cancer, uterine cancer, pancreatic cancer, esophageal cancer, brain cancer, head and neck cancers, ovarian cancer, cervical cancer, testicular cancer, stomach cancer, esophageal cancer, hepatoma, acute lymphoblastic leukemia (ALL), T-ALL, acute myelogenous leukemia (AML), chronic myelogenous leukemia (CML), and chronic lymphocytic leukemia (CLL), salivary carcinomas, or other cancers.

Further embodiments of the present disclosure provide a method of treating, reducing the severity of or preventing a disease selected from the group consisting of sepsis, bone resorption (osteoporosis), cachexia, cancer-related fatigue, psoriasis, systemic-onset juvenile idiopathic arthritis, systemic lupus erythematosus (SLE), mesangial proliferative glomerulonephritis, hyper gammaglobulinemia, Castleman's disease, IgM gammopathy, cardiac myxoma and autoimmune insulin-dependent diabetes.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The polypeptide of the invention can be administered in conjunction with a second active agent. The second active agent can be one or more of 5-aminosalicylic acid, azathioprine, 5-mercaptopurine and a corticosteroid. Dosage regimes for the administration of 5-aminosalicylic acid, azathioprine, 5-mercaptopurine and corticosteroids are well-known to a skilled person.

Production Methods

A further aspect of the invention provides a vector, which comprises a nucleic acid molecule encoding SEQ ID NO: 1 or SEQ ID NO:2 as well as cells comprising said vector. The DNA encoding the amino acid sequence of SEQ ID NO: 1 or SEQ ID NO: 2 may be cloned into the vector such that the signal peptide is linked in-frame to the amino terminus of the amino acid sequence of the antibody chain. The signal peptide can be an immunoglobulin signal peptide or a heterologous signal peptide (i.e., a signal peptide from a non-immunoglobulin protein).

The design of the expression vector, including the selection of regulatory sequences, may depend on such factors as the choice of the host cell to be transformed, the level of expression of protein desired, and so forth. Regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. The host cell may be a mammalian, insect, plant, bacterial, or yeast cell, preferably the cell is a mammalian cell such as a Chinese hamster ovary (CHO) cell. Exemplary CHO cells are (CHO)/dhfr— cells obtained from the European Collection of Cell Cultures (ECACC, No. 9406067).

Figure 7:
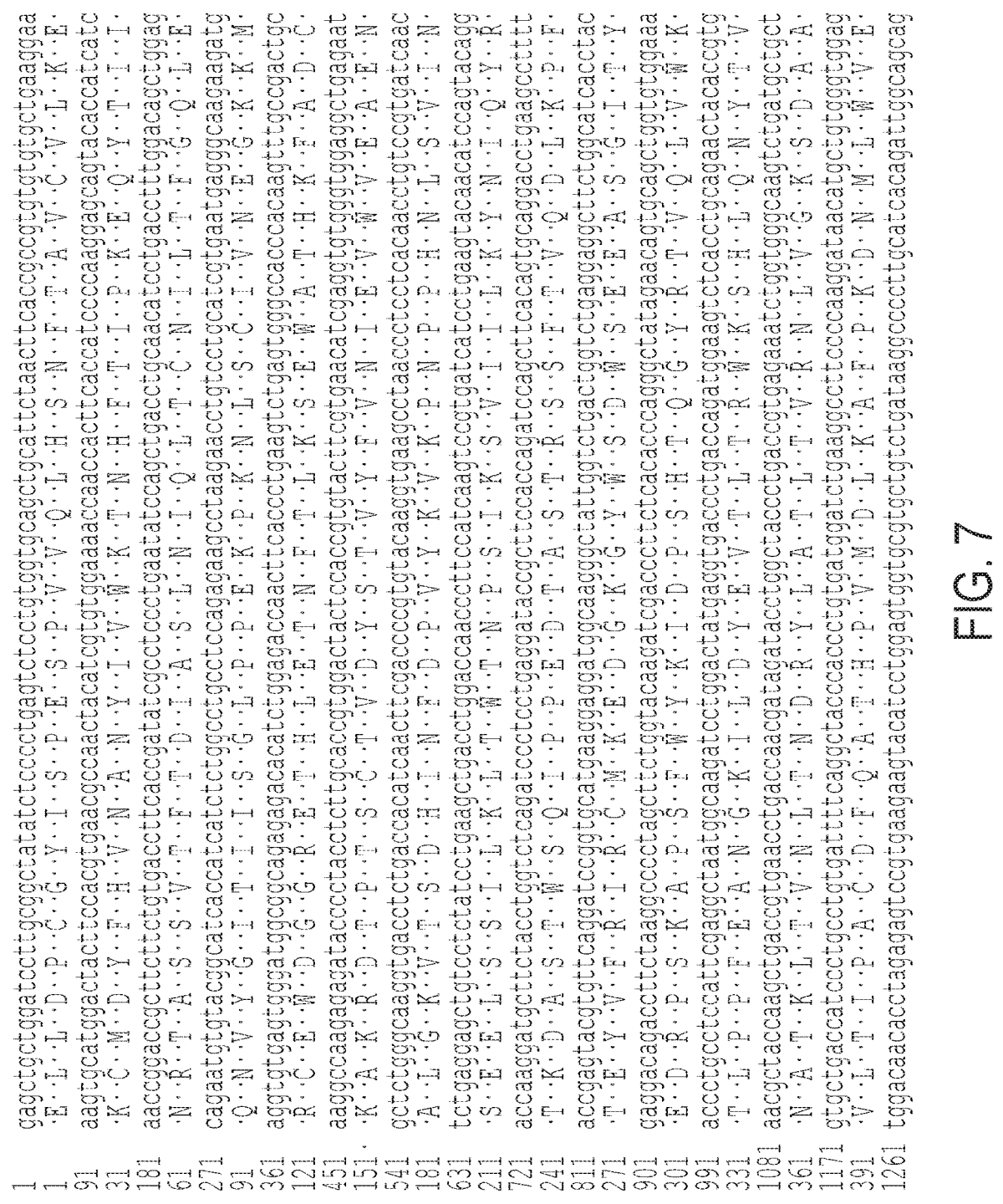

Preferably, the host cell is a CHO cell and the nucleic acid encoding the polypeptide is codon optimized for use in CHO cells. Preferably, the nucleic acid encoding the polypeptide is the sequence depicted in FIG. 3 or FIG. 7.

The disclosure further provides methods for producing the polypeptides of the invention. In one embodiment, a method is provided for producing a dimer comprising two monomers of SEQ ID NO: 1 linked by a disulfide bridge, said method comprising expressing SEQ ID NO: 1 in cells and purifying said polypeptide. Preferably, methods are provided for producing a dimer comprising two monomers of SEQ ID NO: 2 linked by a disulfide bridge, said method comprising expressing SEQ ID NO: 2 in cells and purifying said polypeptide. Methods for introducing nucleic acid vectors are known to a skilled person and include, e.g., electroporation, transfection, and the like. The transfected cells are cultured to allow the cells to express the desired protein. The cells and culture media are then collected and polypeptide dimers are purified, e.g., by chromatography column steps (e.g., MAbSelect Sure, SP Sepharose, Capto Q). The dimer can also be concentrated and/or treated with viral reduction/inactivation steps.

A further aspect of the invention encompasses polypeptide dimers produced by the methods disclosed herein. Preferably, the dimers have the characteristics described herein (e.g., % of galactose-alpha-1,3-galactose per mole polypeptide, sialylation). Dimers produced by the methods can be used to prepare suitable compositions. Said compositions preferably have the characteristics described herein (e.g., low aggregation, truncations).

EXEMPLIFICATION

Example 1

Preparation and Characterization of Peptide 1 (the Polypeptide of SEQ ID NO: 1 in its Active Dimerized Form)
Cloning and Expression of Peptide 1 in CHO/dhfr-Cells CHO/dhfr$^-$ cells were obtained from the European collection of cell cultures (ECACC, No. 9406067). The adherent CHO/dhfr$^-$ cells are deficient in dihydrofolate reductase (DHFR), an enzyme that catalyses the reduction of folate to dihydrofolate and then to tetrahydrofolate. CHO/dhfr$^-$ cells thus display sensitivity to the antifolate drug, methotrexate (MTX).

The CHO/dhfr$^-$ cell line is well characterised and tested. The safety of the CHO/dhfr$^-$ parental cell line as a cell substrate for the production of biopharmaceuticals for human use was confirmed by ECACC (Porton Down, UK) for microbial sterility, mycoplasma, and adventitious viruses according to 21 CFR.
Selection and Construction of the cDNA Sequence The cDNA sequence of Peptide 1 (the polypeptide sequence of SEQ ID NO: 1) was synthesized as a single DNA fragment by GeneArt AG (Regensburg, Germany) using the sequence for the extracellular domain of gp130 (IL6ST, NCBI Gene ID 3572, transcript variant 1 (NP_002175), amino acids 23-617) and Fc domain of human IgG1 (IGHG1, NCBI Gene ID 3500, amino acids 221-447 according to Kabat EU numbering). The sequence was optimized for optimal codon usage in CHO cells. Three well-characterised point mutations were introduced into the lower hinge region of the Fc part.

The cDNA sequence was further modified by replacing the original gp130 signal peptide with a mouse IgG heavy chain signal peptide of known efficacy in CHO cell expression systems. The signal peptide is cleaved off during protein synthesis. The presence of the IgG1 Cys-Pro-Pro-Cys sequence in the Fc region results in the dimerization of two identical gp130-Fc subunits via the sulfhydryl residues on the Fc region, which together form Peptide 1.

Figure 3:
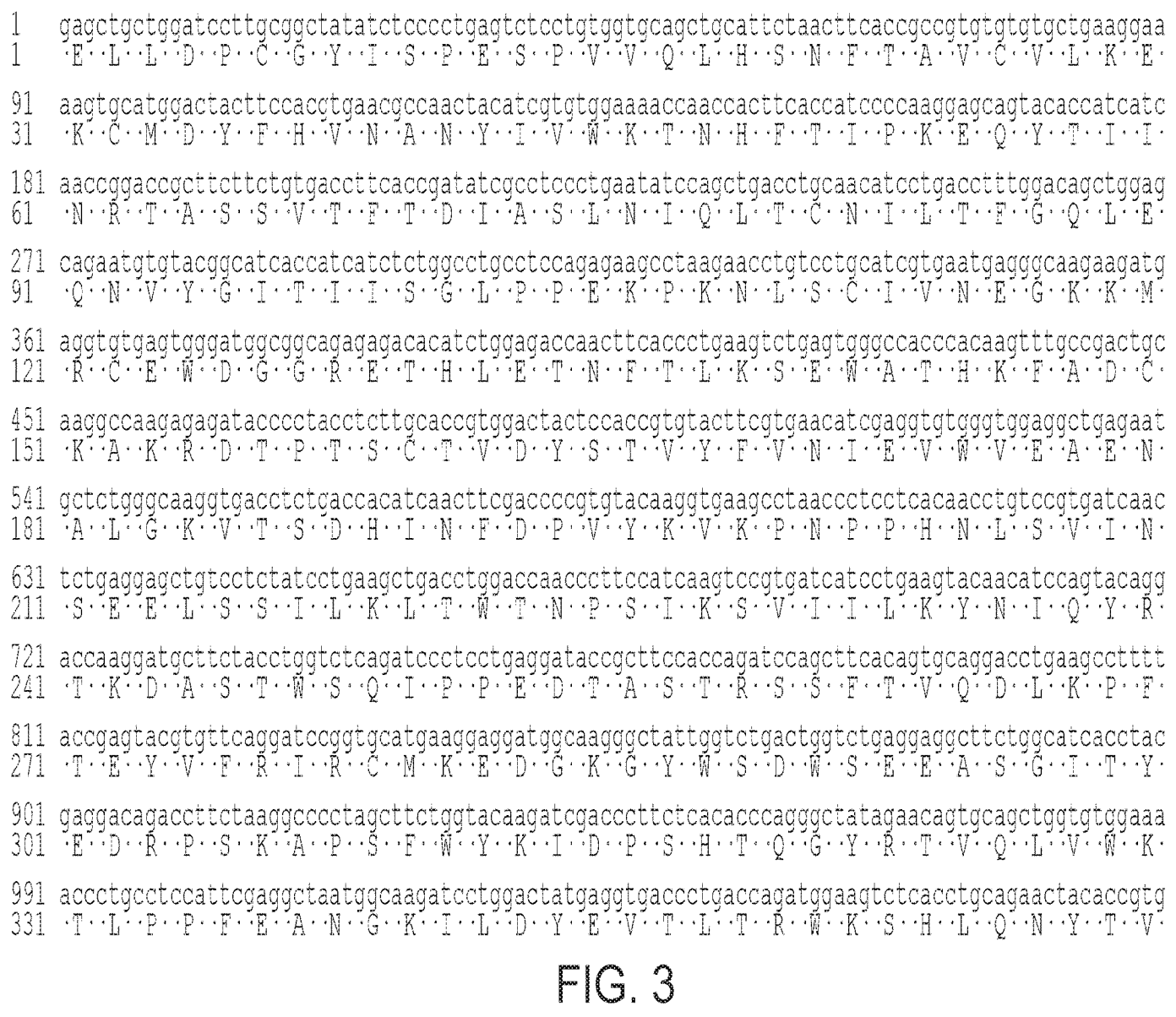
Figure 3:
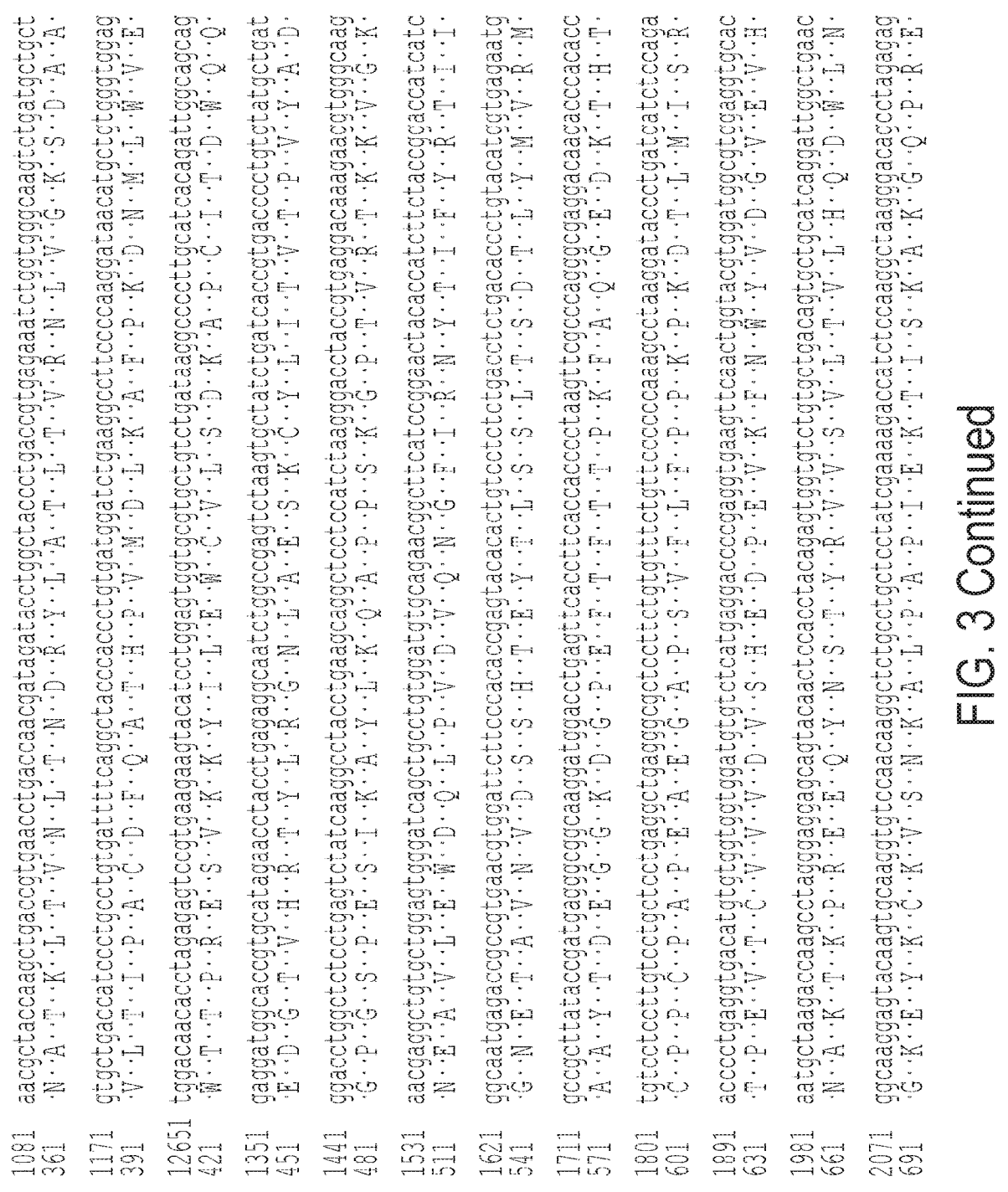

FIG. 3 presents the nucleotide and amino acid sequence of the gp130-Fc subunit used for the formation of Peptide 1.
Construction of the Expression Plasmid for Selection of the Master Cell Bank (MCB)

The Peptide 1 cDNA was cloned into a pANTVhG1 expression vector (Antitope) containing the dhfr gene for transfectant selection with MTX (FIG. 4) as follows: First, the expression vector was digested with MluI and EagI restriction enzymes to permit the insertion of Peptide 1 cDNA. Second, the Peptide 1 coding region was PCR amplified using the OL1425 and OL1426 primers (Table 1) and digested with MluI and EagI restriction enzymes. Third, the digested fragments were gel purified and ligated together to generate the pFER02 expression vector (FIG. 5). The Peptide 1 cDNA was inserted under the control of the cytomegalovirus (CMV) promoter.

Table 2 presents the function of the pFER02 expression elements. FIG. 6 presents the nucleotide sequences of the pFER02 expression elements.

TABLE 1

Oligonucleotide Sequences Used to Amplify the Peptide 1 Coding Region for Cloning into pANTVhG1

| Primer | Sequence (5'-3')* |
|---|---|
| OL1425 | ctgttgct<u>acgcgt</u>gtccactccGAGCTGCTGGA TCCTTGCGGC (SEQ ID NO: 4) |
| OL1426 | gcgggggcttg<u>ccggcc</u>gtggcactcaCTTGCCA GGAGACAGAGACAG (SEQ ID NO: 5) |

*Peptide 1-specific sequences are shown in upper case, vector-specific sequences are shown in lower case and restriction sites are underlined

TABLE 2 pFER02 Expression Elements

| Feature | Function |
|---|---|
| CMV promoter | Immediate-early promoter/enhancer. Permits efficient, high-level expression of the recombinant protein |
| hIgG1 polyA | Human IgG polyadenylation sequence |
| Ampicillin resistance gene (β-lactamase) | Selection of vector in *E. coli* |
| SV40 early promoter and origin | Allows efficient, high-level expression of the neomycin resistance gene and episomal replication in cells expressing SV40 large T antigen |
| DHFR | Selection of stable transfectants in CHO dhfr-cells |
| SV40 polyadenylation signal | Efficient transcription termination and polyadenylation of mRNA |

Cell Line Selection Process Leading to the Final Peptide 1 Producing Clone

The pFER02 vector was linearized with the blunt-end restriction enzyme SspI, which has a single recognition site located in the beta-lactamase gene. The linearized plasmid was transfected into $5 \times 10^6$ CHO/dhfr$^-$ cells using lipid-mediated transfection. Twenty-four hours after transfection, transfected cells were selected in medium supplemented with 5% dialysed foetal calf serum (FCS) and 100 nM methotrexate (MTX). Transfected cells were diluted into this medium at various densities and dispensed into 96-well, flat bottom tissue culture plates. Cells were then incubated in a humidified atmosphere at 5% $CO_2$ and 37° C. Fresh MTX selection medium was added at regular intervals during the incubation time to ensure that MTX levels and nutrient levels remained constant.
Initial Cell Line Selection with MTX Selection For several weeks post transfection, tissue culture plates were examined using a Genetix CloneSelect® Imager, and >2,000 wells were observed to have actively growing colonies. Supernatants from these wells were sampled and assayed for Peptide 1 titre by ELISA. Based on the results of this assay, a total of 105 of the best expressing wells were expanded into 48-well plates. A total of 83 cell lines were selected for expansion into 6-well plates or T-25 flasks; supernatant from each of the cell lines was sampled and assayed for Peptide 1 titre (ELISA). Based on these results, 54 of the best expressing cell lines with optimal growth characteristics were selected for expansion into T-75 or T-175 flasks; supernatants from the confluent flasks were sampled and Peptide 1 titres quantified (ELISA). Comparison of the expression levels between the cell lines allowed for the identification of the 38 best cell lines which were selected for productivity analysis. Productivity was assessed as follows:

$$\text{Productivity(pg/cell/day)} = ((Th-Ti)/((Vh+Vi)/2))/\text{time}$$

Where:
Th is the harvest titre [µg/mL]
Ti is the initial titre [µg/mL]
Vh is the viable cell count at harvest [×$10^6$ cells/mL]
Vi is the initial viable cell count [×$10^6$ cells/mL]
Time is the elapsed time (days) between Ti and Th
Based on productivity results (pg/cell/day), 13 cell lines were selected for gene amplification.

MTX-Driven Gene Amplification for Peptide 1 Cell Line Selection

The 13 selected cell lines were chosen for the first round of gene amplification by selective pressure under increasing concentrations of MTX (0.1-50 M). After 7-10 days, supernatant from each well from each of the 13 cell lines were sampled and assayed for Peptide 1 titre (ELISA). Wells from each cell line with high Peptide 1 expression levels were assessed for productivity (pg/cell/day). A second round of gene amplification was initiated with a total of 16 wells from cell lines that showed significant increases in productivity.

The second round of gene amplification was conducted in the presence of increased MTX concentrations; supernatants from each culture were assayed for Peptide 1 titre (ELISA). Selected wells from each cell line were expanded and productivity was assessed (pg/cell/day); five cell lines with increased productivity in response to increased MTX selection pressure were identified. These five cell lines were progressed to a third round of gene amplification using selection pressure under increased MTX concentration; supernatants from each well were assayed for Peptide 1 titre (ELISA). Selected wells for each cell line were expanded and productivity (pg/cell/day) was assessed; five cell lines demonstrating high Peptide 1 expression were selected.

Limiting Dilution of Clones

Limiting dilution cloning was performed on the five cell lines demonstrating Peptide 1 expression. After one week of incubation, plates were examined using a Genetix CloneSelect® Imager and single colonies were identified. The growth rates of two cell lines during dilution cloning were noted as being particularly slow and so these cell lines were discontinued. In total, from the three remaining cell lines, 58 clonal colonies were selected for expansion, first into 48-well plates and then successively expanded through 12-well plates, T-25 flasks and T-75 flasks in the absence of MTX. Each of the 58 selected clones was then assessed for productivity (pg/cell/day); 16 clones were selected for suspension adaptation and adaptation to growth in a chemically-defined medium.

Adaptation of Cell Lines to Suspension Culture in Chemically Defined Medium

The 16 cell lines were adapted to suspension culture in a chemically-defined medium as follows: selected cell lines in adherent culture were first adapted to suspension both in CHO suspension growth medium (DMEM high glucose, including L-glutamine and sodium pyruvate, 5% dialysed FCS, 20 mg/L L-proline, 1×penicillin/streptomycin, 1% pluronic F68) and then in chemically defined suspension growth medium (CD Opti-CHO® from Life Technologies Ltd. (Paisley, UK), 2.5% dialysed FCS, 0.1×penicillin/streptomycin, 8 mM Glutamax®).

Once adapted to suspension culture, the cell lines were weaned, in stages, into a serum-free chemically-defined suspension growth medium (CD Opti-CHO®, 0.1×penicillin/streptomycin, 8 mM Glutamax®). MTX was omitted from all suspension cultures. The adapted lines were expanded and seed cell banks were prepared. Briefly, cells were expanded to 300 mL total volume and harvested when cell density exceeded 0.85×$10^6$ cells/mL and viability was >90%. A further 3×$10^7$ cells were seeded into a fresh flask containing 70 mL suspension growth medium for growth and productivity analysis. The remaining cells were harvested by centrifugation and resuspended in an appropriate volume of freezing medium to yield a cell suspension at 1×$10^7$ cells/mL. Vials were frozen down to −80° C. The cell bank was then transferred to liquid nitrogen for long-term storage.

The 16 cell lines were further refined down to 5 clones after serum-free adaptation. The 5 clones were assessed for growth (cell density and cell doubling time) and productivity (pg/cell/day), after which 3 clones were selected. One clone was selected to make a master cell bank.

Preparation of the master cell bank (MCB) and working cell bank (WCB) was carried out. One vial from the pre-seed stock was used for the preparation of a 200 vial MCB, and one vial of MCB was used to prepare a 200 vial WCB. In each case, a vial was thawed and the cryopreservation medium removed by centrifugation. The cells were resuspended and propagated in volume in growth medium (CD OptiCHO®/4 mM L-glutamine). Four passages were performed during the creation of MCB and six passages were performed during the creation of WCB.

When sufficient cells were obtained, cells were aliquoted in cryopreservation medium (92.5% CD OptiCHO®/7.5% DMSO) into polypropylene vials (each containing approximately 1.5×$10^7$ viable cells) and cryopreserved by reducing the temperaure to −100° C. over a period of at least 60 minutes in a gradual freezing process. Vials are stored in a vapour phase liquid nitrogen autofill container in a GMP controlled area.

Description of the Drug Substance (DS) Manufacturing Process

A brief description of the Peptide 1 DS manufacturing process is as follows. Cells from a WCB vial are revived and progressively expanded using protein-free medium prior to inoculation into a production bioreactor. Upon completion of the cell culture, cells and cell debris are removed by filtration of the culture.

Purification consists of three chromatography column steps (MAbSelect Sure, SP Sepharose, Capto Q), a concentration and diafiltration step and includes two specific viral reduction/inactivation steps; Triton X-100 (inactivation of enveloped viruses) treatment and a nanofiltration step (removal of enveloped and non-enveloped viruses).

Following concentration and diafiltration, excipients are added for the formulation of the DS. The formulated Peptide 1 is 0.22 µm filtered into containers.

The Sartobind Phenyl column, used in the 10,000 L batch in place of the Capto Q column, is effective in reducing the presence of oligomers. This column was able to reduce the level of oligomeric forms from an average of 2.7% to 1%.

Analytical Methods

Glycan structure analysis was carried out at Procognia Limited (Ashdod, Israel). N-glycans were released from the sample using PNGase F and then labelled with 2-aminobenzamide. Released glycans were treated with or without a series of exoglycosidases in order to generate different glycan forms. Glycans were separated by two-dimensional HPLC analysis (NP-HPLC and WAX) and identified by comparison to a retention time database which was built using in-house-prepared standards separated and analyzed by the same two-dimensional HPLC analysis.

Sialic Acid Content

Ultra high pressure liquid chromatography (UPLC) was used to determine the sialic acid content and confirm peptide identity. The method was conducted using a Acquity UPLC BEH C18 1.7 µm 2.1×50 column and the following mobile phase: 9:7:84/acetonitrile:methanol:water, with a flow rate 0.3 mL/min. The sialic acids were released from the test sample by enzymatic cleavage with sialydase and were thereafter derivatised with a fluorescent label (1,2 diamino 4,5 methylenedioxybenzene dihydrochloride (DMB)). The labelled test sample was separated by UPLC with isocratic elution and fluorescence detection with an excitation wavelength of 373 nm and an emission wavelength of 448 nm. The sialic acid content in the test samples was quantified relative to the N-glycolylneuraminic acid (NGNA) and N-acetlyneuraminic acid (NANA) standards, run as a standard curve. NGNA and NANA sialic acid content is reported as pmol sialic acid/pmol protein.

Sialylation Pattern

Weak anion exchange (WAX)—HPLC was used for determination of the % of the neutral, mono-, di-, tri- and tetra-sialylated glycans. The method entails enzymatic release of the N-glycans from the drug substance with PNGase, fluorescent labelling with 2-aminobenzamide (2-AB), desalting using Ludger DI cartridges. The separation of sialylated glycans was conducted by WAX-HPLC, using a Glyco Sep C column with a 20% acetonitrile/0.5M ammonium format gradient at 40° C. The fluoresce detection was set to at 330 nm excitation and 420 nm emission. Testing of a reference standard was carried out in parallel. The % of the neutral, mono-, di-, tri- and tetra-sialylated glycans were determined from the WAX-HPLC chromatogram and reported.

Purity, SEC

Size-exclusion HPLC (SEC) was used to determine drug substance purity by separating intact active dimers from the SGF and oligomeric forms (comprised primarily of dimers of active dimers). The intact active dimer molecule consists of the two identical glycosylated protein subunits (the gp130 extracellular domain fused to the Fc part of the human IgG1 heavy chain). Samples were separated on the basis of molecular weight using a gel permeation column (TSK $G3000_{SWXL}$) with a flow rate of 1 mL/min and a mobile phase of 0.2 M sodium phosphate pH 7.0. Column eluate was monitored at 280 nm. The intact species is identified by its characteristic retention time; the % purity of the active dimer is expressed as a percentage of the total integrated peak area.

Oligomeric Forms

The percentage of oligomeric forms is determined using the SEC method presented above. The percentage of oligomeric forms is expressed as a percentage of the total integrated peak area.

Single gp130 Form (SGF)

The percentage of SGF was determined using the SEC method presented above. The percentage of SGF is expressed as a percentage of the total integrated peak area.

Results of the analyses are provided in Table 3.

TABLE 3

Characterisation Test Results

| Analysis | Theoretical Value | | Batch 1 (400 L) | Batch 2 (800 L) | Batch 3 (800 L) | Batch 4 (800 L) | Batch 5 (800 L) | Batch 6 (10,000 L) |
|---|---|---|---|---|---|---|---|---|
| Monosaccharide analysis (pmol/pmol Peptide 1) | Fucose | | 7.4 | 7.9 | 7.2 | 6.5 | 6.3 | 6.5 |
| | Glucosamine | | 41.6 | 45.2 | 42.5 | 38.6 | 39.2 | 42.9 |
| | Mannose | | 44.6 | 44.2 | 43.3 | 39.8 | 38.9 | 39.8 |
| | Galactose | | 21.9 | 23.1 | 20.8 | 19.8 | 20.8 | 19.3 |
| Sialylation pattern by WAX-HPLC | Neutral | | 40.9 | 43.2 | 49.7 | 50.9 | 40.8 | 45.2 |
| | Mono-sialylated | | 34.2 | 33.3 | 32.6 | 32.9 | 33.9 | 33.4 |
| | Di-sialylated | | 20.1 | 19.1 | 16.0 | 14.7 | 20.4 | 17.7 |
| | Tri-sialylated | | 4.3 | 4.1 | 1.7 | 1.4 | 4.9 | 3.5 |
| | Tetra-sialylated | | 0.4 | 0.4 | ND | ND | ND | 0.3 |
| | Total core fucose | | 64.1 | 65.8 | 61.4 | 63.3 | 62.4 | 65.6 |
| | Total Sialylation | | 52.2 | 49.6 | 43.0 | 39.8 | 54.1 | 48.0 |
| | Gal-alpha-1,3-Gal | | Not detectable | Not detectable | Not detectable | Not detectable | Not detectable | Not detectable |
| Oxidised forms by RP-HPLC (% area of oxidised peptide vs. non-oxidised peptide in the tested sample) | Report result | Ox 1 | Not tested | ND | ND | 0.035 | 0.013 | 0.009 |
| | | Ox 2 | | 0.198 | 0.175 | 0.172 | 0.177 | 0.158 |
| | | Ox 3 | | 0.127 | 0.123 | 0.119 | 0.119 | 0.123 |
| | | Ox 4 | | ND | ND | ND | ND | ND |
| | | Ox 5 | | ND | ND | ND | ND | ND |
| MW and presence of SGF and Oligomeric forms by SEC-MALS | % Dimer | | 91.2 ± 0.2 | 92.3 ± 0.2 | 93.9 ± 0.1 | 95.2 ± 0.1 | 94.2 ± 0.0 | 95.9 ± 0.0 |
| | % Oligomeric forms | | 4.7 ± 0.1 | 4.3 ± 0.1 | 2.4 ± 0.1 | 1.8 ± 0.1 | 1.9 ± 0.0 | 1.0 ± 0.0 |
| | % SGF | | 4.1 ± 0.1 | 3.4 ± 0.1 | 3.7 ± 0.1 | 2.97 ± 0.1 | 3.9 ± 0.1 | 3.1 ± 0.0 |

Description and Composition of the Drug Product (DP)

The DP is a sterile solution to be administered by i.v. infusion. The DP consists of Peptide 1 at a concentration of 15 mg/mL in an isotonic solution containing 25 mM L-histidine, 200 mM sucrose and 0.1 mg polysorbate 20/mL at pH 7.6. The vials are overlaid with nitrogen for protection against oxidation. The product is intended for single use and storage at −20° C. until thawing for clinical administration.

Composition and Batch Formula

The batch formula for the drug product is presented in Table 4.

TABLE 4

DP Batch Composition

| Component | Amount | Quality standard |
|---|---|---|
| Peptide 1 | 720 g | Ferring specification |
| L-Histidine | 186.18 g | Ph. Eur./USP* |
| Sucrose | 3286.08 g | Ph. Eur./USP* |
| Polysorbate 20 | 4.8 g | Ph. Eur./USP* |
| WFI | ad 49536 g | Ph. Eur./USP* |
| Sodium hydroxide | quantum satis | Ph. Eur./USP* |
| Nitrogen | quantum satis | Ph. Eur./USP* |

*curr. Ed.

Example 2

Clinical Trial 000067 (Single Dose)
Design

This was a single-dose, placebo controlled, single blinded, randomized within dose, parallel group dose-escalating trial. The trial was conducted in two parts, where Part 1 included healthy subjects and Part 2 included patients with CD in clinical remission. The objective was to examine the safety and tolerability, and if possible, to obtain signs of pharmacological effects, after single doses of Peptide 1.

In Part 1, 64 subjects were included, of whom 48 (44 men, 4 women) received active treatment and 16 (all men) received placebo. Seven doses were investigated and administered as an i.v. infusion over 30 minutes (0.75 mg, 7.5 mg, 75 mg), or 1 hour (150 mg, 300 mg, 600 mg, and 750 mg). In addition, 6 subjects received a s.c. dose of 60 mg Peptide 1 and 2 subjects received a s.c. dose of placebo. Peptide 1 was administered at 15 mg/mL in 25 mM histidine, 200 mM sucrose and 0.1 mg/mL polysorbate 20.

In Part 2, 24 patients were included, of whom 18 (11 men, 7 women), received active treatment (75 mg, 300 mg, and 750 mg) and 6 (4 men, 2 women) received placebo, all administered by i.v.

Results

The PK evaluation after i.v. administrations of Peptide 1 showed dose proportionality for both AUC and Cmax in the range 0.75 mg to 750 mg, the Cmax concentrations in plasma ranging from 0.2 to 170 µg/mL (FIG. 3). The clearance was approx. 0.13 L/h, the mean terminal half-life approx. 4.5 days, and the distribution volume approx. 20 L, the latter indicating some extravascular distribution. The s.c. administration of 60 mg Peptide 1 showed a Cmax of 1.1 µg/mL at 2.3 days, and a half-life of 5.0 days. The bioavailability after s.c. administration of Peptide 1 was calculated to be approx. 50%.

Figure 4:
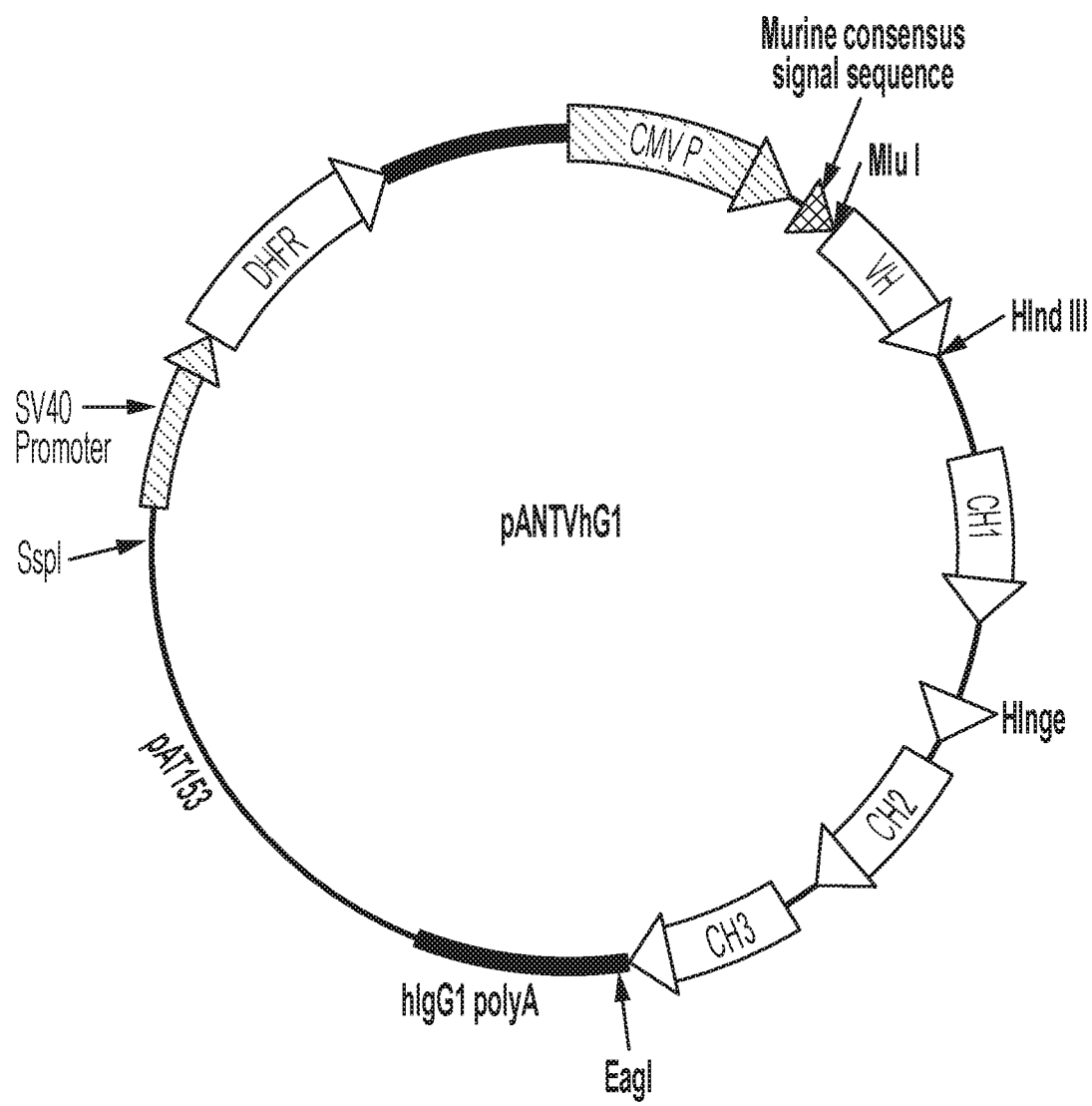
FIG. 4 shows a map of the expression vector pANTVhG1. Elements for human IgG or fusion protein expression and for selection in eukaryotic cells are shown as well as relevant restriction enzyme digestion sites (not to scale). Elements include: CMV P, a cytomegalovirus expression promoter; human IgG1 sequences: VH, CH1, Hinge, CH2, and CH3; hIgG1 poly A, human IgG polyadenylation sequence; pAT153; an expression vector sequence derived from pBR322 that contains a replication origin and Amp gene for bacterial resistance against ampicillin; SV40 promoter sequence; DHFR, dihydrofolate reductase coding sequence; MluI, HindIII, EagI and SspI restriction enzyme digestion sequences; and a murine consensus signal sequence. Details of elements for prokaryotic propagation and selection are not shown.
Figure 5:
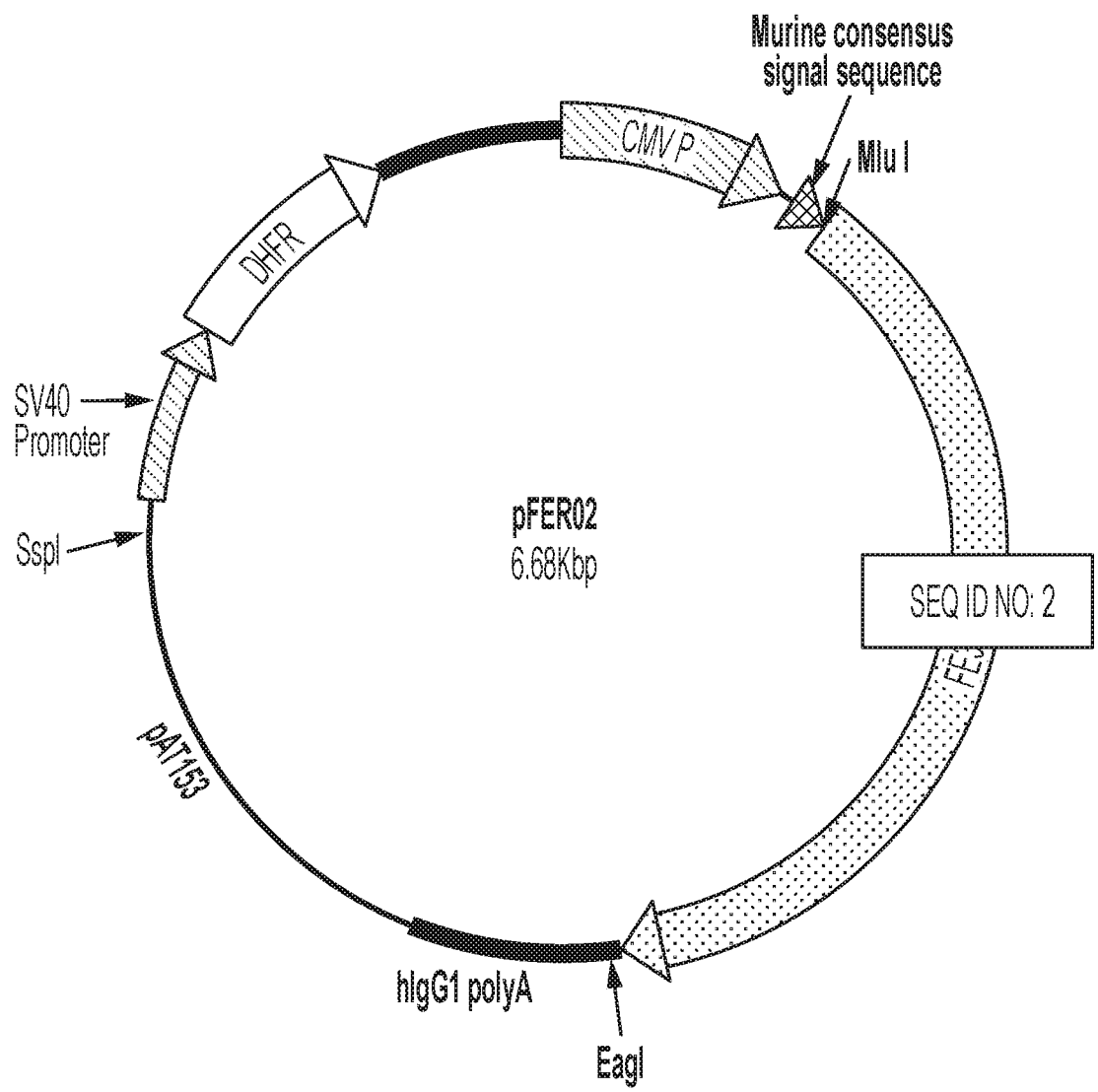
FIG. 5 shows a map of expression vector pFER02. Elements for Peptide 1 expression and for selection in eukaryotic cells as well as relevant restriction enzyme digestion sites are shown (not to scale). Elements include: CMV P, a cytomegalovirus expression promoter; SEQ ID NO: 2, the coding sequence; hIgG1 poly A, human IgG polyadenylation sequence; pAT153; an expression vector sequence derived from pBR322 that contains a replication origin and Amp Gene for bacterial resistance against ampicillin; SV40 promoter sequence; DHFR, dihydrofolate reductase coding sequence; MluI, EagI and SspI restriction enzyme digestion sequences; and a murine consensus signal sequence.

The i.v. administration of 75, 300, and 750 mg to CD patients in remission showed very similar results as for the healthy subjects (FIG. 4). The AUC and Cmax were dose proportional with Cmax concentrations of 16, 76, and 186 µg/mL (16, 77, and 161 µg/mL for healthy subjects). The clearance was approx. 0.13 L/h, the mean terminal half-life approx. 4.6 days, and the distribution volume approx. 22 L.

The safety profile of Peptide 1 was favourable with few adverse events occurring in all treatment groups, including the placebo group, all being mild or moderate. No apparent dose-related trends in incidence or frequency of adverse events were observed. The infusions were discontinued in two subjects, one due to mild (Part 1, 300 mg group) and one due to moderate (Part 2, 75 mg group) infusion reactions.

There were no apparent dose-related trends or treatment-related changes in vital signs, ECG, or clinical chemistry parameters.

One healthy subject in the 300 mg group showed non-neutralizing treatment emergent anti-Peptide 1 antibodies at the follow-up visit 5-6 weeks after administration.

Overall, Peptide was safe and well tolerated when administered intravenously up to 750 mg as a single i.v. dose, and at 60 mg as a single s.c. dose.

Example 3

Clinical Trial 000115 (Multiple Ascending Dose)
Design

This was a placebo controlled, double-blind, within dose-group randomized, parallel group trial with the objective to investigate the safety, tolerability, and pharmacokinetics of multiple ascending doses of Peptide 1. The doses investigated were 75, 300 and 600 mg Peptide 1 administered once a week, for 4 weeks, by i.v. infusion over 30 minutes (75 mg) or 1 hour (300 mg and 600 mg).

Twenty-four (24) healthy subjects were included, of whom 18 (11 men and 7 women) received active treatment and 6 (2 men and 4 women) received placebo.

Results

The PK evaluation showed very close characteristics on the first and last treatment days, and similar to the results in the single-dose study. The AUC and Cmax were dose proportional after first and fourth dosing with Cmax concentrations of 19, 78, and 148 µg/mL after the first dose, and 19, 79, and 142 µg/mL after the fourth dose (16, 77, and 161 µg/mL for single dose in healthy subjects; FIG. 5). The corresponding trough values were 0.66, 2.68, 4.56 µg/mL and 0.98, 3.95 and 7.67 µg/mL for the three dose levels. The mean terminal half-life as calculated after the last dose was approx. 5.5 days.

The safety profile of Peptide 1 was favourable with few adverse events occurring in all treatment groups, including the placebo group, all being mild or moderate. No apparent dose-related trends in incidence or frequency of adverse events were observed. One subject (600 mg group) was withdrawn due to mild infusion reactions.

There were no apparent dose-related trends or treatment related changes in vital signs, ECG, or clinical chemistry parameters.

No anti-Peptide 1 antibodies were detected in any of the subjects.

Overall, Peptide 1 was safe and well tolerated when administered i.v. up to 600 mg once weekly for 4 weeks.

SEQUENCE LISTING

SEQ ID NO: 1

Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
            20                  25                  30

SEQUENCE LISTING

```
Met Asp Tyr Phe His Val Asn Ala Asn Tyr Ile Val Trp Lys Thr Asn
         35                  40                  45

His Phe Thr Ile Pro Lys Glu Gln Tyr Thr Ile Ile Asn Arg Thr Ala
 50                  55                  60

Ser Ser Val Thr Phe Thr Asp Ile Ala Ser Leu Asn Ile Gln Leu Thr
 65                  70                  75                  80

Cys Asn Ile Leu Thr Phe Gly Gln Leu Glu Gln Asn Val Tyr Gly Ile
                 85                  90                  95

Thr Ile Ile Ser Gly Leu Pro Pro Glu Lys Pro Lys Asn Leu Ser Cys
             100                 105                 110

Ile Val Asn Glu Gly Lys Lys Met Arg Cys Glu Trp Asp Gly Gly Arg
             115                 120                 125

Glu Thr His Leu Glu Thr Asn Phe Thr Leu Lys Ser Glu Trp Ala Thr
         130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro Pro His Asn Leu Ser Val
        195                 200                 205

Ile Asn Ser Glu Glu Leu Ser Ser Ile Leu Lys Leu Thr Trp Thr Asn
210                 215                 220

Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
            260                 265                 270

Tyr Val Phe Arg Ile Arg Cys Met Lys Glu Asp Gly Lys Gly Tyr Trp
        275                 280                 285

Ser Asp Trp Ser Glu Glu Ala Ser Gly Ile Thr Tyr Glu Asp Arg Pro
290                 295                 300

Ser Lys Ala Pro Ser Phe Trp Tyr Lys Ile Asp Pro Ser His Thr Gln
305                 310                 315                 320

Gly Tyr Arg Thr Val Gln Leu Val Trp Lys Thr Leu Pro Pro Phe Glu
                325                 330                 335

Ala Asn Gly Lys Ile Leu Asp Tyr Glu Val Thr Leu Thr Arg Trp Lys
            340                 345                 350

Ser His Leu Gln Asn Tyr Thr Val Asn Ala Thr Lys Leu Thr Val Asn
        355                 360                 365

Leu Thr Asn Asp Arg Tyr Leu Ala Thr Leu Thr Val Arg Asn Leu Val
    370                 375                 380

Gly Lys Ser Asp Ala Ala Val Leu Thr Ile Pro Ala Cys Asp Phe Gln
385                 390                 395                 400

Ala Thr His Pro Val Met Asp Leu Lys Ala Phe Pro Lys Asp Asn Met
                405                 410                 415

Leu Trp Val Glu Trp Thr Thr Pro Arg Glu Ser Val Lys Lys Tyr Ile
            420                 425                 430

Leu Glu Trp Cys Val Leu Ser Asp Lys Ala Pro Cys Ile Thr Asp Trp
        435                 440                 445
```

Gln Gln Glu Asp Gly Thr Val His Arg Thr Tyr Leu Arg Gly Asn Leu
        450                 455                 460

Ala Glu Ser Lys Cys Tyr Leu Ile Thr Val Thr Pro Val Tyr Ala Asp
465                 470                 475                 480

Gly Pro Gly Ser Pro Glu Ser Ile Lys Ala Tyr Leu Lys Gln Ala Pro
                485                 490                 495

Pro Ser Lys Gly Pro Thr Val Arg Thr Lys Lys Val Gly Lys Asn Glu
            500                 505                 510

Ala Val Leu Glu Trp Asp Gln Leu Pro Val Asp Val Gln Asn Gly Phe
        515                 520                 525

Ile Arg Asn Tyr Thr Ile Phe Tyr Arg Thr Ile Ile Gly Asn Glu Thr
    530                 535                 540

Ala Val Asn Val Asp Ser Ser His Thr Glu Tyr Thr Leu Ser Ser Leu
545                 550                 555                 560

Thr Ser Asp Thr Leu Tyr Met Val Arg Met Ala Ala Tyr Thr Asp Glu
                565                 570                 575

Gly Gly Lys Asp Gly Pro Glu Phe Thr Phe Thr Thr Pro Lys Phe Ala
            580                 585                 590

Gln Gly Glu Asp Lys Thr His Thr Cys Pro Pro Cys Pro Ala Pro Glu
        595                 600                 605

Ala Glu Gly Ala Pro Ser Val Phe Leu Phe Pro Pro Lys Pro Lys Asp
    610                 615                 620

Thr Leu Met Ile Ser Arg Thr Pro Glu Val Thr Cys Val Val Val Asp
625                 630                 635                 640

Val Ser His Glu Asp Pro Glu Val Lys Phe Asn Trp Tyr Val Asp Gly
                645                 650                 655

Val Glu Val His Asn Ala Lys Thr Lys Pro Arg Glu Glu Gln Tyr Asn
            660                 665                 670

Ser Thr Tyr Arg Val Val Ser Val Leu Thr Val Leu His Gln Asp Trp
        675                 680                 685

Leu Asn Gly Lys Glu Tyr Lys Cys Lys Val Ser Asn Lys Ala Leu Pro
    690                 695                 700

Ala Pro Ile Glu Lys Thr Ile Ser Lys Ala Lys Gly Gln Pro Arg Glu
705                 710                 715                 720

Pro Gln Val Tyr Thr Leu Pro Pro Ser Arg Glu Glu Met Thr Lys Asn
                725                 730                 735

Gln Val Ser Leu Thr Cys Leu Val Lys Gly Phe Tyr Pro Ser Asp Ile
            740                 745                 750

Ala Val Glu Trp Glu Ser Asn Gly Gln Pro Glu Asn Asn Tyr Lys Thr
        755                 760                 765

Thr Pro Pro Val Leu Asp Ser Asp Gly Ser Phe Phe Leu Tyr Ser Lys
    770                 775                 780

Leu Thr Val Asp Lys Ser Arg Trp Gln Gln Gly Asn Val Phe Ser Cys
785                 790                 795                 800

Ser Val Met His Glu Ala Leu His Asn His Tyr Thr Gln Lys Ser Leu
                805                 810                 815

Ser Leu Ser Pro Gly Lys
            820

SEQUENCE LISTING

SEQ ID NO: 2

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Ala Ser Gly Ile
305                 310                 315                 320

Thr Tyr Glu Asp Arg Pro Ser Lys Ala Pro Ser Phe Trp Tyr Lys Ile
            325                 330                 335

Asp Pro Ser His Thr Gln Gly Tyr Arg Thr Val Gln Leu Val Trp Lys
        340                 345                 350

Thr Leu Pro Pro Phe Glu Ala Asn Gly Lys Ile Leu Asp Tyr Glu Val
    355                 360                 365

Thr Leu Thr Arg Trp Lys Ser His Leu Gln Asn Tyr Thr Val Asn Ala
370                 375                 380

Thr Lys Leu Thr Val Asn Leu Thr Asn Asp Arg Tyr Leu Ala Thr Leu
385                 390                 395                 400

SEQUENCE LISTING

```
Thr Val Arg Asn Leu Val Gly Lys Ser Asp Ala Ala Val Leu Thr Ile
            405                 410                 415

Pro Ala Cys Asp Phe Gln Ala Thr His Pro Val Met Asp Leu Lys Ala
        420                 425                 430

Phe Pro Lys Asp Asn Met Leu Trp Val Glu Trp Thr Thr Pro Arg Glu
    435                 440                 445

Ser Val Lys Lys Tyr Ile Leu Glu Trp Cys Val Leu Ser Asp Lys Ala
450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Asp Lys Thr His Thr Cys Pro
    610                 615                 620

Pro Cys Pro Ala Pro Glu Ala Glu Gly Ala Pro Ser Val Phe Leu Phe
625                 630                 635                 640

Pro Pro Lys Pro Lys Asp Thr Leu Met Ile Ser Arg Thr Pro Glu Val
                645                 650                 655

Thr Cys Val Val Val Asp Val Ser His Glu Asp Pro Glu Val Lys Phe
            660                 665                 670

Asn Trp Tyr Val Asp Gly Val Glu Val His Asn Ala Lys Thr Lys Pro
        675                 680                 685

Arg Glu Gly Gln Tyr Asn Ser Thr Tyr Arg Val Val Ser Val Leu Thr
    690                 695                 700

Val Leu His Gln Asp Trp Leu Asn Gly Lys Glu Tyr Lys Cys Lys Val
705                 710                 715                 720

Ser Asn Lys Ala Leu Pro Ala Pro Ile Glu Lys Thr Ile Ser Lys Ala
                725                 730                 735

Lys Gly Gln Pro Arg Glu Pro Gln Val Tyr Thr Leu Pro Pro Ser Arg
            740                 745                 750

Glu Glu Met Thr Lys Asn Gln Val Ser Leu Thr Cys Leu Val Lys Gly
        755                 760                 765

Phe Tyr Pro Ser Asp Ile Ala Val Glu Trp Ser Asn Gly Gln Pro
    770                 775                 780

Glu Asn Asn Tyr Lys Thr Thr Pro Pro Val Leu Asp Ser Asp Gly Ser
785                 790                 795                 800

Phe Phe Leu Tyr Ser Lys Leu Thr Val Asp Lys Ser Arg Trp Gln Gln
                805                 810                 815
```

-continued

SEQUENCE LISTING

```
Gly Asn Val Phe Ser Cys Ser Val Met His Glu Ala Leu His Asn His
            820                 825                 830

Tyr Thr Gln Lys Ser Leu Ser Leu Ser Pro Gly Lys
            835                 840
```

The invention claimed is:

1. A polypeptide dimer comprising two gp130-Fc monomers comprising the amino acid sequence of SEQ ID NO: 1, wherein the monomers comprise the gp130 D6 domain corresponding to the amino acids at positions 585-595 of the amino acid sequence of SEQ ID NO:1, an Fc domain hinge region comprising the amino acids at positions 609-612 of the amino acid sequence of SEQ ID NO:1, and the monomers do not comprise a linker between the gp130 D6 domain and the Fc domain hinge region, wherein:
the polypeptide dimer comprises no greater than 6 mol % of galactose-alpha-1,3-galactose per mole polypeptide.

2. The polypeptide dimer of claim 1, wherein the polypeptide dimer is obtainable by expressing the amino acid sequence of SEQ ID NO: 1 in Chinese Hamster Ovary (CHO) cells, performing multiple rounds of cell line selection, selecting a cell line producing said polypeptide dimer, culturing the cells in culture media, and collecting said polypeptide dimers from said cells and/or cell culture media.

3. A composition comprising the polypeptide dimer of claim 1, wherein:

a. no greater than 5% of the polypeptide dimer is present as an oligomeric aggregate,
b. the composition comprises no greater than 4.0% by weight of polypeptides that are a truncated variation of the polypeptide having the amino acid sequence of SEQ ID NO: 1 with respect to polypeptides having the amino acid sequence of SEQ ID NO: 1, or
c. both a and b.

4. The composition according to claim 3, wherein the composition further comprises a surfactant.

5. The composition of claim 4, wherein the surfactant is a nonionic surfactant.

6. The composition according to claim 3, wherein the composition further comprises a buffering agent and a sugar.

7. The polypeptide dimer according to claim 1, wherein the polypeptide dimer comprises glycans, and wherein a mean of at least 52% of the glycans comprise one or more sialic acid residues.

8. A method for producing a polypeptide dimer according to claim 1, comprising expressing the amino acid sequence of SEQ ID NO: 1 in Chinese Hamster Ovary (CHO) cells, performing multiple rounds of cell line selection, selecting a cell line producing said polypeptide dimer, culturing the cells in culture media, and collecting said polypeptide dimers from said cells and/or cell culture media.

* * * * *

SEQUENCE LISTING

<160> NUMBER OF SEQ ID NOS: 15

<210> SEQ ID NO 1
<211> LENGTH: 822
<212> TYPE: PRT
<213> ORGANISM: Artificial Sequence
<220> FEATURE:
<223> OTHER INFORMATION: gp130-Fc fusion monomer

<400> SEQUENCE: 1

```
Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
            20                  25                  30

Met Asp Tyr Phe His Val Asn Ala Asn Tyr Ile Val Trp Lys Thr Asn
        35                  40                  45

His Phe Thr Ile Pro Lys Glu Gln Tyr Thr Ile Asn Arg Thr Ala
    50                  55                  60

Ser Ser Val Thr Phe Thr Asp Ile Ala Ser Leu Asn Ile Gln Leu Thr
65                  70                  75                  80

Cys Asn Ile Leu Thr Phe Gly Gln Leu Glu Gln Asn Val Tyr Gly Ile
                85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Gly Gly Arg
        115                 120                 125

Glu Thr His Leu Glu Thr Asn Phe Thr Leu Lys Ser Glu Trp Ala Thr
    130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro Pro His Asn Leu Ser Val
        195                 200                 205

Ile Asn Ser Glu Glu Leu Ser Ser Ile Leu Lys Leu Thr Trp Thr Asn
    210                 215                 220

Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
            260                 265                 270

Tyr Val Phe Arg Ile Arg Cys Met Lys Glu Asp Gly Lys Gly Tyr Trp
        275                 280                 285
```

-continued

Ser Asp Trp Ser Glu Glu Ala Ser Gly Ile Thr Tyr Glu Asp Arg Pro
290             295                 300

Ser Lys Ala Pro Ser Phe Trp Tyr Lys Ile Asp Pro Ser His Thr Gln
305             310                 315                 320

Gly Tyr Arg Thr Val Gln Leu Val Trp Lys Thr Leu Pro Pro Phe Glu
                325                 330                 335

Ala Asn Gly Lys Ile Leu Asp Tyr Glu Val Thr Leu Thr Arg Trp Lys
                340                 345                 350

Ser His Leu Gln Asn Tyr Thr Val Asn Ala Thr Lys Leu Thr Val Asn
                355                 360                 365

Leu Thr Asn Asp Arg Tyr Leu Ala Thr Leu Thr Val Arg Asn Leu Val
370             375                 380

Gly Lys Ser Asp Ala Ala Val Leu Thr Ile Pro Ala Cys Asp Phe Gln
385             390                 395                 400

Ala Thr His Pro Val Met Asp Leu Lys Ala Phe Pro Lys Asp Asn Met
                405                 410                 415

Leu Trp Val Glu Trp Thr Thr Pro Arg Glu Ser Val Lys Lys Tyr Ile
                420                 425                 430

Leu Glu Trp Cys Val Leu Ser Asp Lys Ala Pro Cys Ile Thr Asp Trp
                435                 440                 445

Gln Gln Glu Asp Gly Thr Val His Arg Thr Tyr Leu Arg Gly Asn Leu
450                 455                 460

Ala Glu Ser Lys Cys Tyr Leu Ile Thr Val Thr Pro Val Tyr Ala Asp
465                 470                 475                 480

Gly Pro Gly Ser Pro Glu Ser Ile Lys Ala Tyr Leu Lys Gln Ala Pro
                485                 490                 495

Pro Ser Lys Gly Pro Thr Val Arg Thr Lys Lys Val Gly Lys Asn Glu
                500                 505                 510

Ala Val Leu Glu Trp Asp Gln Leu Pro Val Asp Val Gln Asn Gly Phe
                515                 520                 525

Ile Arg Asn Tyr Thr Ile Phe Tyr Arg Thr Ile Ile Gly Asn Glu Thr
530                 535                 540

Ala Val Asn Val Asp Ser Ser His Thr Glu Tyr Thr Leu Ser Ser Leu
545                 550                 555                 560

Thr Ser Asp Thr Leu Tyr Met Val Arg Met Ala Ala Tyr Thr Asp Glu
                565                 570                 575

Gly Gly Lys Asp Gly Pro Glu Phe Thr Phe Thr Thr Pro Lys Phe Ala
                580                 585                 590

Gln Gly Glu Asp Lys Thr His Thr Cys Pro Pro Cys Pro Ala Pro Glu
                595                 600                 605

Ala Glu Gly Ala Pro Ser Val Phe Leu Phe Pro Pro Lys Pro Lys Asp
                610                 615                 620

Thr Leu Met Ile Ser Arg Thr Pro Glu Val Thr Cys Val Val Val Asp
625                 630                 635                 640

Val Ser His Glu Asp Pro Glu Val Lys Phe Asn Trp Tyr Val Asp Gly
                645                 650                 655

Val Glu Val His Asn Ala Lys Thr Lys Pro Arg Glu Glu Gln Tyr Asn
                660                 665                 670

Ser Thr Tyr Arg Val Val Ser Val Leu Thr Val Leu His Gln Asp Trp
                675                 680                 685

Leu Asn Gly Lys Glu Tyr Lys Cys Lys Val Ser Asn Lys Ala Leu Pro
690                 695                 700

```
Ala Pro Ile Glu Lys Thr Ile Ser Lys Ala Lys Gly Gln Pro Arg Glu
705                 710                 715                 720

Pro Gln Val Tyr Thr Leu Pro Pro Ser Arg Glu Glu Met Thr Lys Asn
            725                 730                 735

Gln Val Ser Leu Thr Cys Leu Val Lys Gly Phe Tyr Pro Ser Asp Ile
            740                 745                 750

Ala Val Glu Trp Glu Ser Asn Gly Gln Pro Glu Asn Asn Tyr Lys Thr
            755                 760                 765

Thr Pro Pro Val Leu Asp Ser Asp Gly Ser Phe Phe Leu Tyr Ser Lys
            770                 775                 780

Leu Thr Val Asp Lys Ser Arg Trp Gln Gln Gly Asn Val Phe Ser Cys
785                 790                 795                 800

Ser Val Met His Glu Ala Leu His Asn His Tyr Thr Gln Lys Ser Leu
            805                 810                 815

Ser Leu Ser Pro Gly Lys
            820
```

<210> SEQ ID NO 2
<211> LENGTH: 844
<212> TYPE: PRT
<213> ORGANISM: Artificial Sequence
<220> FEATURE:
<223> OTHER INFORMATION: gp130-Fc fusion monomer

<400> SEQUENCE: 2

```
Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
            85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
            115                 120                 125

Pro Lys Asn Leu Ser Cys Ile Val Asn Glu Gly Lys Lys Met Arg Cys
            130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
            165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
            195                 200                 205

Ser Asp His Ile Asn Phe Asp Pro Val Tyr Lys Val Lys Pro Asn Pro
            210                 215                 220

Pro His Asn Leu Ser Val Ile Asn Ser Glu Glu Leu Ser Ser Ile Leu
225                 230                 235                 240
```

```
Lys Leu Thr Trp Thr Asn Pro Ser Ile Lys Ser Val Ile Ile Leu Lys
                    245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
            275                 280                 285

Leu Lys Pro Phe Thr Glu Tyr Val Phe Arg Ile Arg Cys Met Lys Glu
            290                 295                 300

Asp Gly Lys Gly Tyr Trp Ser Asp Trp Ser Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
                340                 345                 350

Thr Leu Pro Pro Phe Glu Ala Asn Gly Lys Ile Leu Asp Tyr Glu Val
            355                 360                 365

Thr Leu Thr Arg Trp Lys Ser His Leu Gln Asn Tyr Thr Val Asn Ala
            370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
                420                 425                 430

Phe Pro Lys Asp Asn Met Leu Trp Val Glu Trp Thr Thr Pro Arg Glu
                435                 440                 445

Ser Val Lys Lys Tyr Ile Leu Glu Trp Cys Val Leu Ser Asp Lys Ala
            450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
                500                 505                 510

Tyr Leu Lys Gln Ala Pro Pro Ser Lys Gly Pro Thr Val Arg Thr Lys
            515                 520                 525

Lys Val Gly Lys Asn Glu Ala Val Leu Glu Trp Asp Gln Leu Pro Val
            530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
            595                 600                 605

Thr Thr Pro Lys Phe Ala Gln Gly Glu Asp Lys Thr His Thr Cys Pro
            610                 615                 620

Pro Cys Pro Ala Pro Glu Ala Glu Gly Ala Pro Ser Val Phe Leu Phe
625                 630                 635                 640

Pro Pro Lys Pro Lys Asp Thr Leu Met Ile Ser Arg Thr Pro Glu Val
                645                 650                 655
```

```
Thr Cys Val Val Val Asp Val Ser His Glu Asp Pro Glu Val Lys Phe
            660                 665                 670

Asn Trp Tyr Val Asp Gly Val Glu Val His Asn Ala Lys Thr Lys Pro
        675                 680                 685

Arg Glu Glu Gln Tyr Asn Ser Thr Tyr Arg Val Val Ser Val Leu Thr
    690                 695                 700

Val Leu His Gln Asp Trp Leu Asn Gly Lys Glu Tyr Lys Cys Lys Val
705                 710                 715                 720

Ser Asn Lys Ala Leu Pro Ala Pro Ile Glu Lys Thr Ile Ser Lys Ala
                725                 730                 735

Lys Gly Gln Pro Arg Glu Pro Gln Val Tyr Thr Leu Pro Pro Ser Arg
            740                 745                 750

Glu Glu Met Thr Lys Asn Gln Val Ser Leu Thr Cys Leu Val Lys Gly
        755                 760                 765

Phe Tyr Pro Ser Asp Ile Ala Val Glu Trp Glu Ser Asn Gly Gln Pro
    770                 775                 780

Glu Asn Asn Tyr Lys Thr Thr Pro Pro Val Leu Asp Ser Asp Gly Ser
785                 790                 795                 800

Phe Phe Leu Tyr Ser Lys Leu Thr Val Asp Lys Ser Arg Trp Gln Gln
                805                 810                 815

Gly Asn Val Phe Ser Cys Ser Val Met His Glu Ala Leu His Asn His
            820                 825                 830

Tyr Thr Gln Lys Ser Leu Ser Leu Ser Pro Gly Lys
        835                 840

<210> SEQ ID NO 3
<211> LENGTH: 11
<212> TYPE: PRT
<213> ORGANISM: Artificial Sequence
<220> FEATURE:
<223> OTHER INFORMATION: gp130 D6 domain

<400> SEQUENCE: 3

Thr Phe Thr Thr Pro Lys Phe Ala Gln Gly Glu
1               5                   10

<210> SEQ ID NO 4
<211> LENGTH: 44
<212> TYPE: DNA
<213> ORGANISM: Artificial Sequence
<220> FEATURE:
<223> OTHER INFORMATION: primer

<400> SEQUENCE: 4
ctgttgctac gcgtgtccac tccgagctgc tggatccttg cggc                44

<210> SEQ ID NO 5
<211> LENGTH: 48
<212> TYPE: DNA
<213> ORGANISM: Artificial Sequence
<220> FEATURE:
<223> OTHER INFORMATION: primer

<400> SEQUENCE: 5
gcgggggctt gccggccgtg gcactcactt gccaggagac agagacag            48

<210> SEQ ID NO 6
<211> LENGTH: 2466
<212> TYPE: DNA
<213> ORGANISM: Artificial Sequence
```

<220> FEATURE:
<223> OTHER INFORMATION: gp130-Fc subunit
<220> FEATURE:
<221> NAME/KEY: CDS
<222> LOCATION: (1)..(2466)

<400> SEQUENCE: 6

| | | | | | | | | | | | | | | | | |
|---|---|---|---|---|---|---|---|---|---|---|---|---|---|---|---|---|
| gag | ctg | ctg | gat | cct | tgc | ggc | tat | atc | tcc | cct | gag | tct | cct | gtg | gtg | 48 |
| Glu | Leu | Leu | Asp | Pro | Cys | Gly | Tyr | Ile | Ser | Pro | Glu | Ser | Pro | Val | Val | |
| 1 | | | | 5 | | | | | 10 | | | | | 15 | | |

| cag | ctg | cat | tct | aac | ttc | acc | gcc | gtg | tgt | gtg | ctg | aag | gaa | aag | tgc | 96 |
|---|---|---|---|---|---|---|---|---|---|---|---|---|---|---|---|---|
| Gln | Leu | His | Ser | Asn | Phe | Thr | Ala | Val | Cys | Val | Leu | Lys | Glu | Lys | Cys | |
| | | | 20 | | | | | 25 | | | | | 30 | | | |

| atg | gac | tac | ttc | cac | gtg | aac | gcc | aac | tac | atc | gtg | tgg | aaa | acc | aac | 144 |
|---|---|---|---|---|---|---|---|---|---|---|---|---|---|---|---|---|
| Met | Asp | Tyr | Phe | His | Val | Asn | Ala | Asn | Tyr | Ile | Val | Trp | Lys | Thr | Asn | |
| | | | 35 | | | | | 40 | | | | | 45 | | | |

| cac | ttc | acc | atc | ccc | aag | gag | cag | tac | acc | atc | atc | aac | cgg | acc | gct | 192 |
|---|---|---|---|---|---|---|---|---|---|---|---|---|---|---|---|---|
| His | Phe | Thr | Ile | Pro | Lys | Glu | Gln | Tyr | Thr | Ile | Ile | Asn | Arg | Thr | Ala | |
| | 50 | | | | | 55 | | | | | 60 | | | | | |

| tct | tct | gtg | acc | ttc | acc | gat | atc | gcc | tcc | ctg | aat | atc | cag | ctg | acc | 240 |
|---|---|---|---|---|---|---|---|---|---|---|---|---|---|---|---|---|
| Ser | Ser | Val | Thr | Phe | Thr | Asp | Ile | Ala | Ser | Leu | Asn | Ile | Gln | Leu | Thr | |
| 65 | | | | | 70 | | | | | 75 | | | | | 80 | |

| tgc | aac | atc | ctg | acc | ttt | gga | cag | ctg | gag | cag | aat | gtg | tac | ggc | atc | 288 |
|---|---|---|---|---|---|---|---|---|---|---|---|---|---|---|---|---|
| Cys | Asn | Ile | Leu | Thr | Phe | Gly | Gln | Leu | Glu | Gln | Asn | Val | Tyr | Gly | Ile | |
| | | | | 85 | | | | | 90 | | | | | 95 | | |

| acc | atc | atc | tct | ggc | ctg | cct | cca | gag | aag | cct | aag | aac | ctg | tcc | tgc | 336 |
|---|---|---|---|---|---|---|---|---|---|---|---|---|---|---|---|---|
| Thr | Ile | Ile | Ser | Gly | Leu | Pro | Pro | Glu | Lys | Pro | Lys | Asn | Leu | Ser | Cys | |
| | | | 100 | | | | | 105 | | | | | 110 | | | |

| atc | gtg | aat | gag | ggc | aag | aag | atg | agg | tgt | gag | tgg | gat | ggc | ggc | aga | 384 |
|---|---|---|---|---|---|---|---|---|---|---|---|---|---|---|---|---|
| Ile | Val | Asn | Glu | Gly | Lys | Lys | Met | Arg | Cys | Glu | Trp | Asp | Gly | Gly | Arg | |
| | | | 115 | | | | | 120 | | | | | 125 | | | |

| gag | aca | cat | ctg | gag | acc | aac | ttc | acc | ctg | aag | tct | gag | tgg | gcc | acc | 432 |
|---|---|---|---|---|---|---|---|---|---|---|---|---|---|---|---|---|
| Glu | Thr | His | Leu | Glu | Thr | Asn | Phe | Thr | Leu | Lys | Ser | Glu | Trp | Ala | Thr | |
| | | 130 | | | | | 135 | | | | | 140 | | | | |

| cac | aag | ttt | gcc | gac | tgc | aag | gcc | aag | aga | gat | acc | cct | acc | tct | tgc | 480 |
|---|---|---|---|---|---|---|---|---|---|---|---|---|---|---|---|---|
| His | Lys | Phe | Ala | Asp | Cys | Lys | Ala | Lys | Arg | Asp | Thr | Pro | Thr | Ser | Cys | |
| 145 | | | | | 150 | | | | | 155 | | | | | 160 | |

| acc | gtg | gac | tac | tcc | acc | gtg | tac | ttc | gtg | aac | atc | gag | gtg | tgg | gtg | 528 |
|---|---|---|---|---|---|---|---|---|---|---|---|---|---|---|---|---|
| Thr | Val | Asp | Tyr | Ser | Thr | Val | Tyr | Phe | Val | Asn | Ile | Glu | Val | Trp | Val | |
| | | | 165 | | | | | 170 | | | | | 175 | | | |

| gag | gct | gag | aat | gct | ctg | ggc | aag | gtg | acc | tct | gac | cac | atc | aac | ttc | 576 |
|---|---|---|---|---|---|---|---|---|---|---|---|---|---|---|---|---|
| Glu | Ala | Glu | Asn | Ala | Leu | Gly | Lys | Val | Thr | Ser | Asp | His | Ile | Asn | Phe | |
| | | | 180 | | | | | 185 | | | | | 190 | | | |

| gac | ccc | gtg | tac | aag | gtg | aag | cct | aac | cct | cct | cac | aac | ctg | tcc | gtg | 624 |
|---|---|---|---|---|---|---|---|---|---|---|---|---|---|---|---|---|
| Asp | Pro | Val | Tyr | Lys | Val | Lys | Pro | Asn | Pro | Pro | His | Asn | Leu | Ser | Val | |
| | | 195 | | | | | 200 | | | | | 205 | | | | |

| atc | aac | tct | gag | gag | ctg | tcc | tct | atc | ctg | aag | ctg | acc | tgg | acc | aac | 672 |
|---|---|---|---|---|---|---|---|---|---|---|---|---|---|---|---|---|
| Ile | Asn | Ser | Glu | Glu | Leu | Ser | Ser | Ile | Leu | Lys | Leu | Thr | Trp | Thr | Asn | |
| | 210 | | | | | 215 | | | | | 220 | | | | | |

| cct | tcc | atc | aag | tcc | gtg | atc | atc | ctg | aag | tac | aac | atc | cag | tac | agg | 720 |
|---|---|---|---|---|---|---|---|---|---|---|---|---|---|---|---|---|
| Pro | Ser | Ile | Lys | Ser | Val | Ile | Ile | Leu | Lys | Tyr | Asn | Ile | Gln | Tyr | Arg | |
| 225 | | | | | 230 | | | | | 235 | | | | | 240 | |

| acc | aag | gat | gct | tct | acc | tgg | tct | cag | atc | cct | cct | gag | gat | acc | gct | 768 |
|---|---|---|---|---|---|---|---|---|---|---|---|---|---|---|---|---|
| Thr | Lys | Asp | Ala | Ser | Thr | Trp | Ser | Gln | Ile | Pro | Pro | Glu | Asp | Thr | Ala | |
| | | | 245 | | | | | 250 | | | | | 255 | | | |

| tcc | acc | aga | tcc | agc | ttc | aca | gtg | cag | gac | ctg | aag | cct | ttt | acc | gag | 816 |
|---|---|---|---|---|---|---|---|---|---|---|---|---|---|---|---|---|
| Ser | Thr | Arg | Ser | Ser | Phe | Thr | Val | Gln | Asp | Leu | Lys | Pro | Phe | Thr | Glu | |
| | | | 260 | | | | | 265 | | | | | 270 | | | |

| tac | gtg | ttc | agg | atc | cgg | tgc | atg | aag | gag | gat | ggc | aag | ggc | tat | tgg | 864 |
|---|---|---|---|---|---|---|---|---|---|---|---|---|---|---|---|---|
| Tyr | Val | Phe | Arg | Ile | Arg | Cys | Met | Lys | Glu | Asp | Gly | Lys | Gly | Tyr | Trp | |
| | | 275 | | | | | 280 | | | | | 285 | | | | |

-continued

| | |
|---|---|
| tct gac tgg tct gag gag gct tct ggc atc acc tac gag gac aga cct<br>Ser Asp Trp Ser Glu Glu Ala Ser Gly Ile Thr Tyr Glu Asp Arg Pro<br>290                         295                          300 | 912 |
| tct aag gcc cct agc ttc tgg tac aag atc gac cct tct cac acc cag<br>Ser Lys Ala Pro Ser Phe Trp Tyr Lys Ile Asp Pro Ser His Thr Gln<br>305                        310                     315                   320 | 960 |
| ggc tat aga aca gtg cag ctg gtg tgg aaa acc ctg cct cca ttc gag<br>Gly Tyr Arg Thr Val Gln Leu Val Trp Lys Thr Leu Pro Pro Phe Glu<br>                   325                    330                    335 | 1008 |
| gct aat ggc aag atc ctg gac tat gag gtg acc ctg acc aga tgg aag<br>Ala Asn Gly Lys Ile Leu Asp Tyr Glu Val Thr Leu Thr Arg Trp Lys<br>                   340                    345                    350 | 1056 |
| tct cac ctg cag aac tac acc gtg aac gct acc aag ctg acc gtg aac<br>Ser His Leu Gln Asn Tyr Thr Val Asn Ala Thr Lys Leu Thr Val Asn<br>355                         360                     365 | 1104 |
| ctg acc aac gat aga tac ctg gct acc ctg acc gtg aga aat ctg gtg<br>Leu Thr Asn Asp Arg Tyr Leu Ala Thr Leu Thr Val Arg Asn Leu Val<br>     370                    375                    380 | 1152 |
| ggc aag tct gat gct gct gtg ctg acc atc cct gcc tgt gat ttt cag<br>Gly Lys Ser Asp Ala Ala Val Leu Thr Ile Pro Ala Cys Asp Phe Gln<br>385                         390                    395                   400 | 1200 |
| gct acc cac cct gtg atg gat ctg aag gcc ttc ccc aag gat aac atg<br>Ala Thr His Pro Val Met Asp Leu Lys Ala Phe Pro Lys Asp Asn Met<br>                   405                    410                    415 | 1248 |
| ctg tgg gtg gag tgg aca aca cct aga gag tcc gtg aag aag tac atc<br>Leu Trp Val Glu Trp Thr Thr Pro Arg Glu Ser Val Lys Lys Tyr Ile<br>                   420                    425                    430 | 1296 |
| ctg gag tgg tgc gtg ctg tct gat aag gcc cct tgc atc aca gat tgg<br>Leu Glu Trp Cys Val Leu Ser Asp Lys Ala Pro Cys Ile Thr Asp Trp<br>                       435                    440                   445 | 1344 |
| cag cag gag gat ggc acc gtg cat aga acc tac ctg aga ggc aat ctg<br>Gln Gln Glu Asp Gly Thr Val His Arg Thr Tyr Leu Arg Gly Asn Leu<br>                       450                    455                    460 | 1392 |
| gcc gag tct aag tgc tat ctg atc acc gtg acc cct gtg tat gct gat<br>Ala Glu Ser Lys Cys Tyr Leu Ile Thr Val Thr Pro Val Tyr Ala Asp<br>465                         470                    475                   480 | 1440 |
| gga cct ggc tct cct gag tct atc aag gcc tac ctg aag cag gct cct<br>Gly Pro Gly Ser Pro Glu Ser Ile Lys Ala Tyr Leu Lys Gln Ala Pro<br>                       485                    490                    495 | 1488 |
| cca tct aag gga cct acc gtg agg aca aag aag gtg ggc aag aac gag<br>Pro Ser Lys Gly Pro Thr Val Arg Thr Lys Lys Val Gly Lys Asn Glu<br>                 500                    505                    510 | 1536 |
| gct gtg ctg gag tgg gat cag ctg cct gtg gat gtg cag aac ggc ttc<br>Ala Val Leu Glu Trp Asp Gln Leu Pro Val Asp Val Gln Asn Gly Phe<br>               515                    520                    525 | 1584 |
| atc cgg aac tac acc atc ttc tac cgg acc atc atc ggc aat gag acc<br>Ile Arg Asn Tyr Thr Ile Phe Tyr Arg Thr Ile Ile Gly Asn Glu Thr<br>     530                    535                    540 | 1632 |
| gcc gtg aac gtg gat tct tcc cac acc gag tac aca ctg tcc tct ctg<br>Ala Val Asn Val Asp Ser Ser His Thr Glu Tyr Thr Leu Ser Ser Leu<br>545                         550                    555                   560 | 1680 |
| acc tct gac acc ctg tac atg gtg aga atg gcc gct tat acc gat gag<br>Thr Ser Asp Thr Leu Tyr Met Val Arg Met Ala Ala Tyr Thr Asp Glu<br>                   565                    570                    575 | 1728 |
| ggc ggc aag gat gga cct gag ttc acc ttc acc acc cct aag ttc gcc<br>Gly Gly Lys Asp Gly Pro Glu Phe Thr Phe Thr Thr Pro Lys Phe Ala<br>                       580                    585                   590 | 1776 |
| cag ggc gag gac aag acc cac acc tgt cct cct tgt cct gct cct gag<br>Gln Gly Glu Asp Lys Thr His Thr Cys Pro Pro Cys Pro Ala Pro Glu<br>595                         600                    605 | 1824 |

```
gct gag ggc gct cct tct gtg ttt ctg ttc ccc cca aag cct aag gat        1872
Ala Glu Gly Ala Pro Ser Val Phe Leu Phe Pro Pro Lys Pro Lys Asp
610                 615                 620 acc ctg atg atc tcc aga acc cct gag gtg aca tgt gtg gtg gtg gat        1920
Thr Leu Met Ile Ser Arg Thr Pro Glu Val Thr Cys Val Val Val Asp
625                 630                 635                 640 gtg tct cat gag gac ccc gag gtg aag ttc aac tgg tac gtg gat ggc        1968
Val Ser His Glu Asp Pro Glu Val Lys Phe Asn Trp Tyr Val Asp Gly
                645                 650                 655 gtg gag gtg cac aat gct aag acc aag cct agg gag gag cag tac aac        2016
Val Glu Val His Asn Ala Lys Thr Lys Pro Arg Glu Glu Gln Tyr Asn
            660                 665                 670 tcc acc tac aga gtg gtg tct gtg ctg aca gtg ctg cat cag gat tgg        2064
Ser Thr Tyr Arg Val Val Ser Val Leu Thr Val Leu His Gln Asp Trp
        675                 680                 685 ctg aac ggc aag gag tac aag tgc aag gtg tcc aac aag gct ctg cct        2112
Leu Asn Gly Lys Glu Tyr Lys Cys Lys Val Ser Asn Lys Ala Leu Pro
690                 695                 700 gct cct atc gaa aag acc atc tcc aag gct aag gga cag cct aga gag        2160
Ala Pro Ile Glu Lys Thr Ile Ser Lys Ala Lys Gly Gln Pro Arg Glu
705                 710                 715                 720 cct cag gtg tac aca ctg cct cca tct agg gag gag atg acc aag aat        2208
Pro Gln Val Tyr Thr Leu Pro Pro Ser Arg Glu Glu Met Thr Lys Asn
                725                 730                 735 cag gtg tcc ctg acc tgt ctg gtg aag ggc ttc tac cct tct gat atc        2256
Gln Val Ser Leu Thr Cys Leu Val Lys Gly Phe Tyr Pro Ser Asp Ile
            740                 745                 750 gct gtg gag tgg gag tct aat ggc cag ccc gag aac aat tac aag acc        2304
Ala Val Glu Trp Glu Ser Asn Gly Gln Pro Glu Asn Asn Tyr Lys Thr
        755                 760                 765 acc cct cct gtg ctg gat tct gac ggc tcc ttc ttc ctg tac tcc aaa        2352
Thr Pro Pro Val Leu Asp Ser Asp Gly Ser Phe Phe Leu Tyr Ser Lys
770                 775                 780 ctg acc gtg gac aag tct aga tgg cag cag ggc aac gtg ttc tct tgt        2400
Leu Thr Val Asp Lys Ser Arg Trp Gln Gln Gly Asn Val Phe Ser Cys
785                 790                 795                 800 tcc gtg atg cac gag gct ctg cac aat cac tat acc cag aag tcc ctg        2448
Ser Val Met His Glu Ala Leu His Asn His Tyr Thr Gln Lys Ser Leu
                805                 810                 815 tct ctg tct cct ggc aag                                                2466
Ser Leu Ser Pro Gly Lys
            820

<210> SEQ ID NO 7
<211> LENGTH: 822
<212> TYPE: PRT
<213> ORGANISM: Artificial Sequence
<220> FEATURE:
<223> OTHER INFORMATION: Synthetic Construct

<400> SEQUENCE: 7

Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
                20                  25                  30

Met Asp Tyr Phe His Val Asn Ala Asn Tyr Ile Val Trp Lys Thr Asn
            35                  40                  45

His Phe Thr Ile Pro Lys Glu Gln Tyr Thr Ile Ile Asn Arg Thr Ala
        50                  55                  60
```

```
Ser Ser Val Thr Phe Thr Asp Ile Ala Ser Leu Asn Ile Gln Leu Thr
 65                  70                  75                  80

Cys Asn Ile Leu Thr Phe Gly Gln Leu Glu Gln Asn Val Tyr Gly Ile
                 85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Gly Gly Arg
        115                 120                 125

Glu Thr His Leu Glu Thr Asn Phe Thr Leu Lys Ser Glu Trp Ala Thr
    130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
                180                 185                 190

Asp Pro Val Tyr Lys Val Lys Pro Asn Pro His Asn Leu Ser Val
                195                 200                 205

Ile Asn Ser Glu Glu Leu Ser Ser Ile Leu Lys Leu Thr Trp Thr Asn
210                 215                 220

Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
                260                 265                 270

Tyr Val Phe Arg Ile Arg Cys Met Lys Glu Asp Gly Lys Gly Tyr Trp
            275                 280                 285

Ser Asp Trp Ser Glu Glu Ala Ser Gly Ile Thr Tyr Glu Asp Arg Pro
290                 295                 300

Ser Lys Ala Pro Ser Phe Trp Tyr Lys Ile Asp Pro Ser His Thr Gln
305                 310                 315                 320

Gly Tyr Arg Thr Val Gln Leu Val Trp Lys Thr Leu Pro Pro Phe Glu
                325                 330                 335

Ala Asn Gly Lys Ile Leu Asp Tyr Glu Val Thr Leu Thr Arg Trp Lys
                340                 345                 350

Ser His Leu Gln Asn Tyr Thr Val Asn Ala Thr Lys Leu Thr Val Asn
        355                 360                 365

Leu Thr Asn Asp Arg Tyr Leu Ala Thr Leu Thr Val Arg Asn Leu Val
    370                 375                 380

Gly Lys Ser Asp Ala Ala Val Leu Thr Ile Pro Ala Cys Asp Phe Gln
385                 390                 395                 400

Ala Thr His Pro Val Met Asp Leu Lys Ala Phe Pro Lys Asp Asn Met
                405                 410                 415

Leu Trp Val Glu Trp Thr Thr Pro Arg Glu Ser Val Lys Lys Tyr Ile
            420                 425                 430

Leu Glu Trp Cys Val Leu Ser Asp Lys Ala Pro Cys Ile Thr Asp Trp
            435                 440                 445

Gln Gln Glu Asp Gly Thr Val His Arg Thr Tyr Leu Arg Gly Asn Leu
    450                 455                 460

Ala Glu Ser Lys Cys Tyr Leu Ile Thr Val Thr Pro Val Tyr Ala Asp
465                 470                 475                 480
```

Gly Pro Gly Ser Pro Glu Ser Ile Lys Ala Tyr Leu Lys Gln Ala Pro
            485                 490                 495

Pro Ser Lys Gly Pro Thr Val Arg Thr Lys Lys Val Gly Lys Asn Glu
        500                 505                 510

Ala Val Leu Glu Trp Asp Gln Leu Pro Val Asp Val Gln Asn Gly Phe
            515                 520                 525

Ile Arg Asn Tyr Thr Ile Phe Tyr Arg Thr Ile Ile Gly Asn Glu Thr
        530                 535                 540

Ala Val Asn Val Asp Ser Ser His Thr Glu Tyr Thr Leu Ser Ser Leu
545                 550                 555                 560

Thr Ser Asp Thr Leu Tyr Met Val Arg Met Ala Ala Tyr Thr Asp Glu
            565                 570                 575

Gly Gly Lys Asp Gly Pro Glu Phe Thr Phe Thr Thr Pro Lys Phe Ala
            580                 585                 590

Gln Gly Glu Asp Lys Thr His Thr Cys Pro Cys Pro Ala Pro Glu
        595                 600                 605

Ala Glu Gly Ala Pro Ser Val Phe Leu Phe Pro Lys Pro Lys Asp
        610                 615                 620

Thr Leu Met Ile Ser Arg Thr Pro Glu Val Thr Cys Val Val Val Asp
625                 630                 635                 640

Val Ser His Glu Asp Pro Glu Val Lys Phe Asn Trp Tyr Val Asp Gly
            645                 650                 655

Val Glu Val His Asn Ala Lys Thr Lys Pro Arg Glu Glu Gln Tyr Asn
            660                 665                 670

Ser Thr Tyr Arg Val Val Ser Val Leu Thr Val Leu His Gln Asp Trp
        675                 680                 685

Leu Asn Gly Lys Glu Tyr Lys Cys Lys Val Ser Asn Lys Ala Leu Pro
        690                 695                 700

Ala Pro Ile Glu Lys Thr Ile Ser Lys Ala Lys Gly Gln Pro Arg Glu
705                 710                 715                 720

Pro Gln Val Tyr Thr Leu Pro Pro Ser Arg Glu Glu Met Thr Lys Asn
            725                 730                 735

Gln Val Ser Leu Thr Cys Leu Val Lys Gly Phe Tyr Pro Ser Asp Ile
            740                 745                 750

Ala Val Glu Trp Glu Ser Asn Gly Gln Pro Glu Asn Asn Tyr Lys Thr
        755                 760                 765

Thr Pro Pro Val Leu Asp Ser Asp Gly Ser Phe Phe Leu Tyr Ser Lys
        770                 775                 780

Leu Thr Val Asp Lys Ser Arg Trp Gln Gln Gly Asn Val Phe Ser Cys
785                 790                 795                 800

Ser Val Met His Glu Ala Leu His Asn His Tyr Thr Gln Lys Ser Leu
            805                 810                 815

Ser Leu Ser Pro Gly Lys
            820

<210> SEQ ID NO 8
<211> LENGTH: 584
<212> TYPE: DNA
<213> ORGANISM: cytamegalovirus

<400> SEQUENCE: 8
attaatagta atcaattacg gggtcattag ttcatagccc atatatggag ttccgcgtta     60
cataacttac ggtaaatggc ccgcctggct gaccgcccaa cgacccccgc ccattgacgt    120
caataatgac gtatgttccc atagtaacgc caataggggac tttccattga cgtcaatggg    180

```
tggagtattt acggtaaact gcccacttgg cagtacatca agtgtatcat atgccaagta      240
cgccccctat tgacgtcaat gacggtaaat ggcccgcctg gcattatgcc cagtacatga      300
ccttatggga ctttcctact tggcagtaca tctacgtatt agtcatcgct attaccatgg      360
tgatgcggtt ttggcagtac atcaatgggc gtggatagcg gtttgactca cggggatttc      420
caagtctcca ccccattgac gtcaatggga gtttgttttg gcaccaaaat caacgggact      480
ttccaaaatg tcgtaacaac tccgccccat tgacgcaaat gggcggtagg cgtgtacggt      540
gggaggtcta taagcaga gctcgtttag tgaaccgtca gatc                        584
```

<210> SEQ ID NO 9
<211> LENGTH: 327
<212> TYPE: DNA
<213> ORGANISM: Homo sapiens

<400> SEQUENCE: 9

```
gtgccacggc cggcaagccc ccgctccccg ggctctcgcg gtcgcacgag gatgcttggc       60
acgtaccccg tctacatact tcccaggcac ccagcatgga aataaagcac ccaccactgc      120
cctgggcccc tgcgagactg tgatggttct ttccacgggt caggccgagt ctgaggcctg      180
agtggcatga gggaggcaga gtgggtccca ctgtccccac actggcccag gctgtgcagg      240
tgtgcctggg ccgcctaggg tggggctcag ccaggggctg ccctcggcag ggtgggggat      300
ttgccagcgt ggccctccct ccagcag                                          327
```

<210> SEQ ID NO 10
<211> LENGTH: 861
<212> TYPE: DNA
<213> ORGANISM: Salmonella paratyphi

<400> SEQUENCE: 10

```
ttaccaatgc ttaatcagtg aggcacctat ctcagcgatc tgtctatttc gttcatccat       60
agttgcctga ctccccgtcg tgtagataac tacgatacgg gagggcttac catctggccc      120
cagtgctgca atgataccgc gagacccacg ctcaccggct ccagatttat cagcaataaa      180
ccagccagcc ggaagggccg agcgcagaag tggtcctgca actttatccg cctccatcca      240
gtctattaat tgttgccggg aagctagagt aagtagttcg ccagttaata gtttgcgcaa      300
cgttgttgcc attgctacag gcatcgtggt gtcacgctcg tcgtttggta tggcttcatt      360
cagctccggt tcccaacgat caaggcgagt tacatgatcc cccatgttgt gcaaaaaagc      420
ggttagctcc ttcggtcctc cgatcgttgt cagaagtaag ttggccgcag tgttatcact      480
catggttatg gcagcactgc ataattctct tactgtcatg ccatccgtaa gatgcttttc      540
tgtgactggt gagtactcaa ccaagtcatt ctgagaatag tgtatgcggc gaccgagttg      600
ctcttgcccg gcgtcaatac gggataatac cgcgccacat agcagaactt taaaagtgct      660
catcattgga aaacgttctt cggggcgaaa actctcaagg atcttaccgc tgttgagatc      720
cagttcgatg taacccactc gtgcacccaa ctgatcttca gcatctttta ctttcaccag      780
cgtttctggg tgagcaaaaa caggaaggca aaatgccgca aaaagggaa taagggcgac      840 acggaaatgt tgaatactca t                                                861
```

<210> SEQ ID NO 11
<211> LENGTH: 356
<212> TYPE: DNA
<213> ORGANISM: Simian virus 40

<400> SEQUENCE: 11

```
cacgaggccc tattgattat tgactagcta gtgtggaatg tgtgtcagtt agggtgtgga      60
aagtccccag gctccccagc aggcagaagt atgcaaagca tgcatctcaa ttagtcagca    120
accaggtgtg aaagtcccc aggctcccca gcaggcagaa gtatgcaaag catgcatctc     180
aattagtcag caaccatagt cccgcccta actccgccca tcccgcccct aactccgccc     240
agttccgccc attctccgcc ccatggctga ctaattttt ttatttatgc agaggccgag     300
gccgcctcgg cctctgagct attccagaag tagtgaggag ctttttgg aggcct          356
```

<210> SEQ ID NO 12
<211> LENGTH: 564
<212> TYPE: DNA
<213> ORGANISM: cytomegalovirus

<400> SEQUENCE: 12

```
atggttcgac cattgaactg catcgtcgcc gtgtcccaaa atatggggat tggcaagaac      60
ggagaccgac cctggcctcc gctcaggaac gagttcaagt acttccaaag aatgaccaca   120
acctcttcag tggaaggtaa acagaatctg gtgattatgg gtaggaaaac ctggttctcc   180
attcctgaga gaatcgacc tttaaaggac agaattaata tagttctcag tagagaactc    240
aaagaaccac cacgaggagc tcatttttctt gccaaaagtt tggatgatgc cttaagactt   300
attgaacaac cggaattggc aagtaaagta gacatggttt ggatagtcgg aggcagttct   360
gtttaccagg aagccatgaa tcaaccaggc cacctcagac tctttgtgac aaggatcatg   420
caggaatttg aaagtgacac cttttttccca gaaattgatt tggggaaata taaacttctc   480
ccagaatacc caggcgtcct ctctgaggtc caggaggaaa aaggcatcaa gtataagttt   540
gaagtctacg agaagaaaga ctaa                                           564
```

<210> SEQ ID NO 13
<211> LENGTH: 323
<212> TYPE: DNA
<213> ORGANISM: Simian virus 40

<400> SEQUENCE: 13

```
caggaagatg cttttcaagtt ctctgctccc ctcctaaagc tatgcatttt tataagacca      60
tgggactttt gctggctta gatcataatc agccatacca catttgtaga ggttttactt    120
gctttaaaaa acctcccaca cctccccctg aacctgaaac ataaaatgaa tgcaattgtt   180
gttgttaact tgtttattgc agcttctaat ggttacaaat aaagcaatag catcacaaat   240
ttcacaaata aagcatttt ttcactgcat tctagttgtg gtttgtccaa actcatcaat    300
gtatcttatc atgtctggat cgg                                             323
```

<210> SEQ ID NO 14
<211> LENGTH: 2466
<212> TYPE: DNA
<213> ORGANISM: Artificial Sequence
<220> FEATURE:
<223> OTHER INFORMATION: gp130-Fc subunit
<220> FEATURE:
<221> NAME/KEY: CDS
<222> LOCATION: (1)..(2466)

<400> SEQUENCE: 14

```
gag ctg ctg gat cct tgc ggc tat atc tcc cct gag tct cct gtg gtg      48
Glu Leu Leu Asp Pro Cys Gly Tyr Ile Ser Pro Glu Ser Pro Val Val
1               5                   10                  15
```

| | | |
|---|---|---|
| cag ctg cat tct aac ttc acc gcc gtg tgt gtg ctg aag gaa aag tgc<br>Gln Leu His Ser Asn Phe Thr Ala Val Cys Val Leu Lys Glu Lys Cys<br>20 25 30 | 96 | |
| atg gac tac ttc cac gtg aac gcc aac tac atc gtg tgg aaa acc aac<br>Met Asp Tyr Phe His Val Asn Ala Asn Tyr Ile Val Trp Lys Thr Asn<br>35 40 45 | 144 | |
| cac ttc acc atc ccc aag gag cag tac acc atc atc aac cgg acc gct<br>His Phe Thr Ile Pro Lys Glu Gln Tyr Thr Ile Ile Asn Arg Thr Ala<br>50 55 60 | 192 | |
| tct tct gtg acc ttc acc gat atc gcc tcc ctg aat atc cag ctg acc<br>Ser Ser Val Thr Phe Thr Asp Ile Ala Ser Leu Asn Ile Gln Leu Thr<br>65 70 75 80 | 240 | |
| tgc aac atc ctg acc ttt gga cag ctg gag cag aat gtg tac ggc atc<br>Cys Asn Ile Leu Thr Phe Gly Gln Leu Glu Gln Asn Val Tyr Gly Ile<br>85 90 95 | 288 | |
| acc atc atc tct ggc ctg cct cca gag aag cct aag aac ctg tcc tgc<br>Thr Ile Ile Ser Gly Leu Pro Pro Glu Lys Pro Lys Asn Leu Ser Cys<br>100 105 110 | 336 | |
| atc gtg aat gag ggc aag aag atg agg tgt gag tgg gat ggc ggc aga<br>Ile Val Asn Glu Gly Lys Lys Met Arg Cys Glu Trp Asp Gly Gly Arg<br>115 120 125 | 384 | |
| gag aca cat ctg gag acc aac ttc acc ctg aag tct gag tgg gcc acc<br>Glu Thr His Leu Glu Thr Asn Phe Thr Leu Lys Ser Glu Trp Ala Thr<br>130 135 140 | 432 | |
| cac aag ttt gcc gac tgc aag gcc aag aga gat acc cct acc tct tgc<br>His Lys Phe Ala Asp Cys Lys Ala Lys Arg Asp Thr Pro Thr Ser Cys<br>145 150 155 160 | 480 | |
| acc gtg gac tac tcc acc gtg tac ttc gtg aac atc gag gtg tgg gtg<br>Thr Val Asp Tyr Ser Thr Val Tyr Phe Val Asn Ile Glu Val Trp Val<br>165 170 175 | 528 | |
| gag gct gag aat gct ctg ggc aag gtg acc tct gac cac atc aac ttc<br>Glu Ala Glu Asn Ala Leu Gly Lys Val Thr Ser Asp His Ile Asn Phe<br>180 185 190 | 576 | |
| gac ccc gtg tac aag gtg aag cct aac cct cct cac aac ctg tcc gtg<br>Asp Pro Val Tyr Lys Val Lys Pro Asn Pro Pro His Asn Leu Ser Val<br>195 200 205 | 624 | |
| atc aac tct gag gag ctg tcc tct atc ctg aag ctg acc tgg acc aac<br>Ile Asn Ser Glu Glu Leu Ser Ser Ile Leu Lys Leu Thr Trp Thr Asn<br>210 215 220 | 672 | |
| cct tcc atc aag tcc gtg atc atc ctg aag tac aac atc cag tac agg<br>Pro Ser Ile Lys Ser Val Ile Ile Leu Lys Tyr Asn Ile Gln Tyr Arg<br>225 230 235 240 | 720 | |
| acc aag gat gct tct acc tgg tct cag atc cct cct gag gat acc gct<br>Thr Lys Asp Ala Ser Thr Trp Ser Gln Ile Pro Pro Glu Asp Thr Ala<br>245 250 255 | 768 | |
| tcc acc aga tcc agc ttc aca gtg cag gac ctg aag cct ttt acc gag<br>Ser Thr Arg Ser Ser Phe Thr Val Gln Asp Leu Lys Pro Phe Thr Glu<br>260 265 270 | 816 | |
| tac gtg ttc agg atc cgg tgc atg aag gag gat ggc aag ggc tat tgg<br>Tyr Val Phe Arg Ile Arg Cys Met Lys Glu Asp Gly Lys Gly Tyr Trp<br>275 280 285 | 864 | |
| tct gac tgg tct gag gag gct tct ggc atc acc tac gag gac aga cct<br>Ser Asp Trp Ser Glu Glu Ala Ser Gly Ile Thr Tyr Glu Asp Arg Pro<br>290 295 300 | 912 | |
| tct aag gcc cct agc ttc tgg tac aag atc gac cct tct cac acc cag<br>Ser Lys Ala Pro Ser Phe Trp Tyr Lys Ile Asp Pro Ser His Thr Gln<br>305 310 315 320 | 960 | |
| ggc tat aga aca gtg cag ctg gtg tgg aaa acc ctg cct cca ttc gag<br>Gly Tyr Arg Thr Val Gln Leu Val Trp Lys Thr Leu Pro Pro Phe Glu<br>325 330 335 | 1008 | |

```
gct aat ggc aag atc ctg gac tat gag gtg acc ctg acc aga tgg aag      1056
Ala Asn Gly Lys Ile Leu Asp Tyr Glu Val Thr Leu Thr Arg Trp Lys
            340                 345                 350 tct cac ctg cag aac tac acc gtg aac gct acc aag ctg acc gtg aac      1104
Ser His Leu Gln Asn Tyr Thr Val Asn Ala Thr Lys Leu Thr Val Asn
    355                 360                 365 ctg acc aac gat aga tac ctg gct acc ctg acc gtg aga aat ctg gtg      1152
Leu Thr Asn Asp Arg Tyr Leu Ala Thr Leu Thr Val Arg Asn Leu Val
370                 375                 380 ggc aag tct gat gct gct gtg ctg acc atc cct gcc tgt gat ttt cag      1200
Gly Lys Ser Asp Ala Ala Val Leu Thr Ile Pro Ala Cys Asp Phe Gln
385                 390                 395                 400 gct acc cac cct gtg atg gat ctg aag gcc ttc ccc aag gat aac atg      1248
Ala Thr His Pro Val Met Asp Leu Lys Ala Phe Pro Lys Asp Asn Met
                405                 410                 415 ctg tgg gtg gag tgg aca aca cct aga gag tcc gtg aag aag tac atc      1296
Leu Trp Val Glu Trp Thr Thr Pro Arg Glu Ser Val Lys Lys Tyr Ile
        420                 425                 430 ctg gag tgg tgc gtg ctg tct gat aag gcc cct tgc atc aca gat tgg      1344
Leu Glu Trp Cys Val Leu Ser Asp Lys Ala Pro Cys Ile Thr Asp Trp
            435                 440                 445 cag cag gag gat ggc acc gtg cat aga acc tac ctg aga ggc aat ctg      1392
Gln Gln Glu Asp Gly Thr Val His Arg Thr Tyr Leu Arg Gly Asn Leu
450                 455                 460 gcc gag tct aag tgc tat ctg atc acc gtg acc cct gtg tat gct gat      1440
Ala Glu Ser Lys Cys Tyr Leu Ile Thr Val Thr Pro Val Tyr Ala Asp
465                 470                 475                 480 gga cct ggc tct cct gag tct atc aag gcc tac ctg aag cag gct cct      1488
Gly Pro Gly Ser Pro Glu Ser Ile Lys Ala Tyr Leu Lys Gln Ala Pro
                485                 490                 495 cca tct aag gga cct acc gtg agg aca aag aag gtg ggc aag aac gag      1536
Pro Ser Lys Gly Pro Thr Val Arg Thr Lys Lys Val Gly Lys Asn Glu
        500                 505                 510 gct gtg ctg gag tgg gat cag ctg cct gtg gat gtg cag aac ggc ttc      1584
Ala Val Leu Glu Trp Asp Gln Leu Pro Val Asp Val Gln Asn Gly Phe
            515                 520                 525 atc cgg aac tac acc atc ttc tac cgg acc atc atc ggc aat gag acc      1632
Ile Arg Asn Tyr Thr Ile Phe Tyr Arg Thr Ile Ile Gly Asn Glu Thr
530                 535                 540 gcc gtg aac gtg gat tct tcc cac acc gag tac aca ctg tcc tct ctg      1680
Ala Val Asn Val Asp Ser Ser His Thr Glu Tyr Thr Leu Ser Ser Leu
545                 550                 555                 560 acc tct gac acc ctg tac atg gtg aga atg gcc gct tat acc gat gag      1728
Thr Ser Asp Thr Leu Tyr Met Val Arg Met Ala Ala Tyr Thr Asp Glu
                565                 570                 575 ggc ggc aag gat gga cct gag ttc acc ttc acc acc cct aag ttc gcc      1776
Gly Gly Lys Asp Gly Pro Glu Phe Thr Phe Thr Thr Pro Lys Phe Ala
        580                 585                 590 cag ggc gag gac aag acc cac acc tgt cct cct tgt cct gct cct gag      1824
Gln Gly Glu Asp Lys Thr His Thr Cys Pro Pro Cys Pro Ala Pro Glu
            595                 600                 605 gct gag ggc gct cct tct gtg ttt ctg ttc ccc cca aag cct aag gat      1872
Ala Glu Gly Ala Pro Ser Val Phe Leu Phe Pro Pro Lys Pro Lys Asp
610                 615                 620 acc ctg atg atc tcc aga acc cct gag gtg aca tgt gtg gtg gtg gat      1920
Thr Leu Met Ile Ser Arg Thr Pro Glu Val Thr Cys Val Val Val Asp
625                 630                 635                 640 gtg tct cat gag gac ccc gag gtg aag ttc aac tgg tac gtg gat ggc      1968
Val Ser His Glu Asp Pro Glu Val Lys Phe Asn Trp Tyr Val Asp Gly
                645                 650                 655
```

```
gtg gag gtg cac aat gct aag acc aag cct agg gag gag cag tac aac    2016
Val Glu Val His Asn Ala Lys Thr Lys Pro Arg Glu Glu Gln Tyr Asn
            660                 665                 670 tcc acc tac aga gtg gtg tct gtg ctg aca gtg ctg cat cag gat tgg    2064
Ser Thr Tyr Arg Val Val Ser Val Leu Thr Val Leu His Gln Asp Trp
        675                 680                 685 ctg aac ggc aag gag tac aag tgc aag gtg tcc aac aag gct ctg cct    2112
Leu Asn Gly Lys Glu Tyr Lys Cys Lys Val Ser Asn Lys Ala Leu Pro
    690                 695                 700 gct cct atc gaa aag acc atc tcc aag gct aag gga cag cct aga gag    2160
Ala Pro Ile Glu Lys Thr Ile Ser Lys Ala Lys Gly Gln Pro Arg Glu
705                 710                 715                 720 cct cag gtg tac aca ctg cct cca tct agg gag gag atg acc aag aat    2208
Pro Gln Val Tyr Thr Leu Pro Pro Ser Arg Glu Glu Met Thr Lys Asn
                725                 730                 735 cag gtg tcc ctg acc tgt ctg gtg aag ggc ttc tac cct tct gat atc    2256
Gln Val Ser Leu Thr Cys Leu Val Lys Gly Phe Tyr Pro Ser Asp Ile
            740                 745                 750 gct gtg gag tgg gag tct aat ggc cag ccc gag aac aat tac aag acc    2304
Ala Val Glu Trp Glu Ser Asn Gly Gln Pro Glu Asn Asn Tyr Lys Thr
        755                 760                 765 acc cct cct gtg ctg gat tct gac ggc tcc ttc ttc ctg tac tcc aaa    2352
Thr Pro Pro Val Leu Asp Ser Asp Gly Ser Phe Phe Leu Tyr Ser Lys
    770                 775                 780 ctg acc gtg gac aag tct aga tgg cag cag ggc aac gtg ttc tct tgt    2400
Leu Thr Val Asp Lys Ser Arg Trp Gln Gln Gly Asn Val Phe Ser Cys
785                 790                 795                 800 tcc gtg atg cac gag gct ctg cac aat cac tat acc cag aag tcc ctg    2448
Ser Val Met His Glu Ala Leu His Asn His Tyr Thr Gln Lys Ser Leu
                805                 810                 815 tct ctg tct cct ggc aag                                            2466
Ser Leu Ser Pro Gly Lys
            820

<210> SEQ ID NO 15
<211> LENGTH: 822
<212> TYPE: PRT
<213> ORGANISM: Artificial Sequence
<220> FEATURE:
<223> OTHER INFORMATION: Synthetic Construct

<400> SEQUENCE: 15

Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
            20                  25                  30

Met Asp Tyr Phe His Val Asn Ala Asn Tyr Ile Val Trp Lys Thr Asn
        35                  40                  45

His Phe Thr Ile Pro Lys Glu Gln Tyr Thr Ile Asn Arg Thr Ala
    50                  55                  60

Ser Ser Val Thr Phe Thr Asp Ile Ala Ser Leu Asn Ile Gln Leu Thr
65                  70                  75                  80

Cys Asn Ile Leu Thr Phe Gly Gln Leu Glu Gln Asn Val Tyr Gly Ile
                85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Gly Gly Arg
        115                 120                 125
```

-continued

```
Glu Thr His Leu Glu Thr Asn Phe Thr Leu Lys Ser Glu Trp Ala Thr
        130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro His Asn Leu Ser Val
        195                 200                 205

Ile Asn Ser Glu Glu Leu Ser Ser Ile Leu Lys Leu Thr Trp Thr Asn
210                 215                 220

Pro Ser Ile Lys Ser Val Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
            260                 265                 270

Tyr Val Phe Arg Ile Arg Cys Met Lys Glu Asp Gly Lys Gly Tyr Trp
        275                 280                 285

Ser Asp Trp Ser Glu Glu Ala Ser Gly Ile Thr Tyr Glu Asp Arg Pro
290                 295                 300

Ser Lys Ala Pro Ser Phe Trp Tyr Lys Ile Asp Pro Ser His Thr Gln
305                 310                 315                 320

Gly Tyr Arg Thr Val Gln Leu Val Trp Lys Thr Leu Pro Pro Phe Glu
                325                 330                 335

Ala Asn Gly Lys Ile Leu Asp Tyr Glu Val Thr Leu Thr Arg Trp Lys
            340                 345                 350

Ser His Leu Gln Asn Tyr Thr Val Asn Ala Thr Lys Leu Thr Val Asn
        355                 360                 365

Leu Thr Asn Asp Arg Tyr Leu Ala Thr Leu Thr Val Arg Asn Leu Val
370                 375                 380

Gly Lys Ser Asp Ala Ala Val Leu Thr Ile Pro Ala Cys Asp Phe Gln
385                 390                 395                 400

Ala Thr His Pro Val Met Asp Leu Lys Ala Phe Pro Lys Asp Asn Met
                405                 410                 415

Leu Trp Val Glu Trp Thr Thr Pro Arg Glu Ser Val Lys Lys Tyr Ile
            420                 425                 430

Leu Glu Trp Cys Val Leu Ser Asp Lys Ala Pro Cys Ile Thr Asp Trp
        435                 440                 445

Gln Gln Glu Asp Gly Thr Val His Arg Thr Tyr Leu Arg Gly Asn Leu
450                 455                 460

Ala Glu Ser Lys Cys Tyr Leu Ile Thr Val Thr Pro Val Tyr Ala Asp
465                 470                 475                 480

Gly Pro Gly Ser Pro Glu Ser Ile Lys Ala Tyr Leu Lys Gln Ala Pro
                485                 490                 495

Pro Ser Lys Gly Pro Thr Val Arg Thr Lys Lys Val Gly Lys Asn Glu
            500                 505                 510

Ala Val Leu Glu Trp Asp Gln Leu Pro Val Asp Val Gln Asn Gly Phe
        515                 520                 525

Ile Arg Asn Tyr Thr Ile Phe Tyr Arg Thr Ile Ile Gly Asn Glu Thr
530                 535                 540
```

-continued

```
Ala Val Asn Val Asp Ser Ser His Thr Glu Tyr Thr Leu Ser Ser Leu
545                 550                 555                 560

Thr Ser Asp Thr Leu Tyr Met Val Arg Met Ala Ala Tyr Thr Asp Glu
                565                 570                 575

Gly Gly Lys Asp Gly Pro Glu Phe Thr Phe Thr Thr Pro Lys Phe Ala
            580                 585                 590

Gln Gly Glu Asp Lys Thr His Thr Cys Pro Pro Cys Pro Ala Pro Glu
        595                 600                 605

Ala Glu Gly Ala Pro Ser Val Phe Leu Phe Pro Pro Lys Pro Lys Asp
        610                 615                 620

Thr Leu Met Ile Ser Arg Thr Pro Glu Val Thr Cys Val Val Val Asp
625                 630                 635                 640

Val Ser His Glu Asp Pro Glu Val Lys Phe Asn Trp Tyr Val Asp Gly
                645                 650                 655

Val Glu Val His Asn Ala Lys Thr Lys Pro Arg Glu Glu Gln Tyr Asn
                660                 665                 670

Ser Thr Tyr Arg Val Val Ser Val Leu Thr Val Leu His Gln Asp Trp
            675                 680                 685

Leu Asn Gly Lys Glu Tyr Lys Cys Lys Val Ser Asn Lys Ala Leu Pro
690                 695                 700

Ala Pro Ile Glu Lys Thr Ile Ser Lys Ala Lys Gly Gln Pro Arg Glu
705                 710                 715                 720

Pro Gln Val Tyr Thr Leu Pro Pro Ser Arg Glu Glu Met Thr Lys Asn
                725                 730                 735

Gln Val Ser Leu Thr Cys Leu Val Lys Gly Phe Tyr Pro Ser Asp Ile
            740                 745                 750

Ala Val Glu Trp Glu Ser Asn Gly Gln Pro Glu Asn Asn Tyr Lys Thr
        755                 760                 765

Thr Pro Pro Val Leu Asp Ser Asp Gly Ser Phe Phe Leu Tyr Ser Lys
        770                 775                 780

Leu Thr Val Asp Lys Ser Arg Trp Gln Gln Gly Asn Val Phe Ser Cys
785                 790                 795                 800

Ser Val Met His Glu Ala Leu His Asn His Tyr Thr Gln Lys Ser Leu
                805                 810                 815

Ser Leu Ser Pro Gly Lys
                820
```